(12) United States Patent
Matsumoto et al.

(10) Patent No.: US 11,499,140 B2
(45) Date of Patent: *Nov. 15, 2022

(54) METHOD FOR PRODUCING PANCREATIC ENDOCRINE CELLS, AND TRANSDIFFERENTIATION AGENT

(71) Applicant: Juntendo Educational Foundation, Tokyo (JP)

(72) Inventors: Masahito Matsumoto, Tokyo (JP); Yasushi Okazaki, Tokyo (JP); Izumi Sugahara, Saitama (JP)

(73) Assignee: JUNTENDO EDUCATIONAL FOUNDATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/770,910

(22) PCT Filed: Oct. 28, 2016

(86) PCT No.: PCT/JP2016/082095
§ 371 (c)(1),
(2) Date: Apr. 25, 2018

(87) PCT Pub. No.: WO2017/073740
PCT Pub. Date: May 4, 2017

(65) Prior Publication Data
US 2018/0312812 A1 Nov. 1, 2018

(30) Foreign Application Priority Data
Oct. 29, 2015 (JP) .............................. JP2015-212563

(51) Int. Cl.
| | |
|---|---|
| *C12N 5/074* | (2010.01) |
| *C12N 5/071* | (2010.01) |
| *C07K 14/47* | (2006.01) |
| *C07K 14/435* | (2006.01) |
| *C12N 15/10* | (2006.01) |

(52) U.S. Cl.
CPC .......... *C12N 5/0696* (2013.01); *C07K 14/435* (2013.01); *C07K 14/4702* (2013.01); *C12N 5/0676* (2013.01); *C12N 15/1068* (2013.01); *C12N 2501/13* (2013.01); *C12N 2501/60* (2013.01); *C12N 2501/998* (2013.01); *C12N 2506/1307* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| | | |
|---|---|---|
| 8,927,277 B2 | 1/2015 | Yamanaka et al. |
| 10,214,728 B2 | 2/2019 | Matsumoto et al. |
| 10,793,832 B2 | 10/2020 | Matsumoto et al. |
| 2003/0077259 A1 | 4/2003 | Levine et al. |
| 2009/0280096 A1 | 11/2009 | Kubo et al. |
| 2011/0112015 A1 | 5/2011 | Julier et al. |
| 2013/0029423 A1 | 1/2013 | Yamanaka et al. |
| 2017/0211046 A1 | 1/2016 | Matsumoto et al. |

FOREIGN PATENT DOCUMENTS

| | | | |
|---|---|---|---|
| JP | 2003245067 A | 9/2003 | |
| JP | 2005506072 A | 3/2005 | |
| JP | 2009533047 A | 9/2009 | |
| JP | 2013-519371 | 5/2013 | |
| WO | 03078636 A1 | 9/2003 | |
| WO | WO-2011102531 A1 * | 8/2011 | ........... C12N 5/0696 |
| WO | 2016/002937 | 1/2016 | |

OTHER PUBLICATIONS

Zhou et al Nature, 627-632 (Year: 2008).*
Yang et al Diabetologia, 54(10): 2595-2605 Y (Year: 2011).*
Ngo et al.,The protein Folding Problem and Tertiary Structure Prediction, pp. 492-495 (Year: 1994).*
Skolnick et al Trends in Biotech,18, 34-39 (Year: 2000).*
Kojima et al Cell Mol Life Sci. ;74(12):2203-2215 (Year: 2017).*
Lalit et al., Cell Stem Cell 18, 354-367 (Year: 2016).*
Cyranoski, Nature, 516:162-164 (Year: 2014).*
Patel et al., Stem Cell Rev., 6(3): 367-380 (Year: 2010).*
Kang et al Histol Histopathol. 25(11): 1481-1496, 1-25 (Year: 2010).*
Rychlik et al. Nuc. Acids Res. 18:6409-6412 (Year: 1990).*
Kang et al Histol Histopathol. 25(11): 1481-1496 (Year: 2010).*
Heremans The Journal of Cell Biology, vol. 159, No. 2, 303-311 (Year: 2002).*
Lee et al eLife ;2:e00940, 1-22 (Year: 2013).*
Zhou, Q, et al., "In Vivo Reprogramming of Adult Pancreatic Exocrine Cells . . . ", Nature, 2008, vol. 455, p. 627-632, ISSN 0028-0836.

(Continued)

*Primary Examiner* — Anoop K Singh
(74) *Attorney, Agent, or Firm* — Morgan, Lewis & Bockius LLP

(57) ABSTRACT

A method for producing pancreatic endocrine cells, including introducing (A), (B), (C), or (D) into somatic cells: (A) mutated GLIS1 gene having 85%-sequence-identity to base sequence of SEQ ID NO: 1 or 2 or gene product(s) thereof, Neurogenin3 gene or gene product(s) thereof, Pdx1 gene or gene product(s) thereof, and MafA gene or gene product(s) thereof; (B) mutated GLIS1 gene having 85%-sequence-identity to base sequence of SEQ ID NO: 1 or 2 or gene product(s) thereof, Neurogenin3 gene or gene product(s) thereof, and Pdx1 gene or gene product(s) thereof (C) GLIS1 gene or gene product(s) thereof, Neurogenin3 gene or gene product(s) thereof, Pdx1 gene or gene product(s) thereof, and MafA gene or gene product(s) thereof and (D) mutated GLIS1 gene having 85%-sequence-identity to base sequence of SEQ ID NO: 1 or 2 or gene product(s) thereof, Neurogenin3 gene or gene product(s) thereof, and MafA gene or gene product(s) thereof.

2 Claims, 7 Drawing Sheets

Specification includes a Sequence Listing.

(56) References Cited

OTHER PUBLICATIONS

Extended European Search Report dated Mar. 29, 2019 (6 pgs).
Momoko Maekawa et al: "Direct reprogramming of somatic cells is promoted by maternal transcription factor Glis1", Nature, vol. 474, No. 7350, Jun. 1, 2011 (Jun. 1, 2011), pp. 225-229, XP055572349, London ISSN: 0028-0836, DOI: 10.1038/nature10106.
Official Communication dated Jun. 18, 2021 for European Patent Application No. 16859968.6.
Kim, Y., et al., "Identification of Glis1, a Novel Gli related, Kruppel like Zinc Finger Protein Containing Transactivation and Repressor Functions", Journal of Biological Chemistry, vol. 277, No. 34, Aug. 16, 2002, pp. 30901 30913.
Kang HS., et al., Mol. Cell. Biol., Dec. 2009. vol. 29, No. 24, p. 6366-6379.
Kim Y.S., et al., Mol. Cells, Aug. 2012. vol. 34, No. 2, p. 193-200.
International Search Report issued in international Application No. PCT/JP2015/069296 dated Sep. 8, 2015.
Written Opinion issued in international Application No. PCT/JP2015/069296 dated Sep. 8, 2015.
IPRP Chapter II in PCTJP2015069296 dated Dec. 9, 2015 with English translation.
Extended European Search Report issued in European Application No. 15815940.0 dated Dec. 13, 2017.
Akinci et al.: "Reprogramming of pancreatic exocrine cells towards a beta(beta) cell character using Pdxl, Ngn3 and MafA", Biochemical Journal, Portland Press Ltd, GB, vol. 442, No. Part 3, Mar. 15, 2012(Mar. 15, 2012), pp. 539-550, XP002725446, ISSN: 0264-6021, DOI: 10.1042/BJ20111678.
Mfopou Josue Kunjom et al: "Recent advances and prospects in the differentiation of pancreatic cells from human embryonic stem cell", DIAB, American Diabetes Association, US, vol. 59, No. 9, Sep. 1, 2010 (Sep. 1, 2010), pp. 2094-2101, XP009138606, ISSN: 0012-1797, DOI: 10.2337/DBIO-0439.
David W. Scoville et al: "GLISI-3: emerging roles in reprogramming, stem and progenitor cell differentiation and maintenance", Stem Cell Investigation, vol. 4, No. 9, Sep. 27, 2017(Sep. 27, 2017), pp. 80-80, XP055431048, DOI: 10.21037/sci.2017.09.01.
Yasuoka Y, Matsumoto M, Yagi K, Okazaki Y, Evolutionary history of GLIS genes illuminates their roles in cell reprogramming and ciliogenesis. Mol. Biol. Evol., 37(1), 100 109, 2019 doi:10.1093/molbev/msz205.
Japanese Office Action of JP 2016-531476 dated Nov. 26, 2019 with Machine English translation.
Japanese Office Action of JP 2016-531476 dated Jul. 14, 2020 with Machine English translation.
Japanese Office Action of JP 2020-171341 dated Oct. 19, 2021 with English translation.
U.S. Office Action of U.S. Appl. No. 15/323,576 dated Apr. 20, 2018.
U.S. Office Action of U.S. Appl. No. 16/243,865 dated Oct. 3, 2019.
Non-Final Office Action dated Sep. 7, 2022 in connection with U.S. Appl. No. 16/883,572.

\* cited by examiner

SEQUENCE LISTING

```
<160> NUMBER OF SEQ ID NOS: 10

<210> SEQ ID NO 1
<211> LENGTH: 1290
<212> TYPE: DNA
<213> ORGANISM: Artificial Sequence
<220> FEATURE:
<223> OTHER INFORMATION: Synthesized sequence

<400> SEQUENCE: 1
```

| | |
|---|---|
| atggttgccg gtcggcaggc atgccgctgg gtggactgct gcgcagccta cgagcagcag | 60 |
| gaggagctgg tgcggcacat cgagaagagc cacatcgacc agcgcaaggg cgaagacttc | 120 |
| acctgcttct gggccgggtg tgtgcggcgc tacaagccct caatgcccg ctacaagctg | 180 |
| ctcatccaca tgagggtaca ctcaggcgag aagcccaaca agtgcatgtt cgaaggctgc | 240 |
| agtaaagcct tttcccgtct ggagaacctg aagatccatc tgcggagcca cacaggcgag | 300 |
| aaaccatacc tgtgccagca cccaggctgc agaaggcct tcagcaactc cagcgaccgt | 360 |
| gccaagcacc aacgcaccca cctcgacacg aagccatatg cttgtcagat ccctggctgc | 420 |
| tccaagcgct acacggaccc cagctccctc cgcaagcacg tgaaggccca ctcagccaaa | 480 |
| gagcagcagg tgcgtaagaa gctgcacaca ggtgccgacc cagaggctga tgttctgtcc | 540 |
| gagtgtctgt ccctgcagca gctccaagca tccacactgt tgccggccag cagagggaag | 600 |
| ggcagccaaa ccctgagcca ggagctcctc ccaggtgtgt atcctggctc cgtcaccca | 660 |
| caaaacgggc ttgcttcagg catcctgtcc ccctcccacg atgtcccttc caggcaccac | 720 |
| ccactggagg tccccactgg ttcccaccac caccgtcccc ctctgccac agctgagagc | 780 |
| accagggatg gcctggggcc cagtctcctt tcacccatgg tcagcccact gaaggggctt | 840 |
| ggtcccccac cgctaccacc agcctcccag agtcagtctc caggggggaca gtcattctct | 900 |
| acagtcccca gcaagcctac ctacccatcc ttccaaagcc caccacctct gcccagcccc | 960 |
| caaggctacc aaggcagttt ccattccatc cagaactgct cccctacgc tgactgctac | 1020 |
| cgggccactg agccagcagc ctccagggat ggactggtgg gtgatgccca cggtttcaac | 1080 |
| cccttgcgac ccagcacata ctccagcctc agcacacctt tatccgcacc aggctacgag | 1140 |
| accctggcag aaacgccgtg tccccagcg ctgcagccac agccagctga agacctggta | 1200 |
| cctagtggtc ctgaggactg tggcttcttc cccaatgggg cctttgacca ctgtctgagt | 1260 |
| cacatcccgt ccatctacac tgacacctga | 1290 |

<210> SEQ ID NO 2
<211> LENGTH: 1299
<212> TYPE: DNA
<213> ORGANISM: Artificial Sequence
<220> FEATURE:
<223> OTHER INFORMATION: Synthesized sequence

<400> SEQUENCE: 2

| | |
|---|---|
| atggtggtgg ccgggcggca ggcgtgccgc tgggtggact gctgtgcagc ctatgagcag | 60 |
| caggaggagc tggtgcggca catcgagaag agccacatcg accagcgcaa gggcgaggac | 120 |
| ttcacctgct ctgggctgg ctgcgtgcgc cgctacaagc ccttcaacgc ccgctacaag | 180 |
| ctgctcatcc acatgcgagt gcactcgggc gagaagccca caagtgcat gtttgaaggc | 240 |
| tgcagcaagg ccttctcacg gctggagaac ctcaagatcc acctgaggag ccacacgggc | 300 |
| gagaagccgt acctgtgcca gcacccgggt gccagaaggc cttcagcaa ctccagcgac | 360 |
| cgcgccaagc accagcgcac ccacctagac acgaagccgt acgcctgtca gatccctggc | 420 |
| tgctccaagc gctacacaga ccccagctcc ctccgcaagc acgtcaaggc ccattcagcc | 480 |
| aaagagcagc aggtgcgtaa gaagctgcat gcgggccctg acaccgaggc cgacgtcctg | 540 |
| accgagtgtc tggtcctgca gcagctccac acgtccacac agctggctgc cagcgacggc | 600 |
| aagggtggct gtggcctggg ccaggagctg ctcccaggtg tgtatcctgg ctccatcacc | 660 |
| ccccataacg gacttgcatc gggcctcctg ccccagcgc acgacgtacc ttccaggcac | 720 |
| caccgctgg atgccaccac cagttcccac caccatctgt cccctctgcc catggctgag | 780 |

-continued

```
agcacccggg atgggttggg gcccggcctc ctctcaccaa tagtcagccc cctgaagggg    840
ctggggccac cgccgctgcc cccatcctct cagagccatt ctccgggggg ccagcccttc    900
cccacactcc ccagcaagcc gtcctaccca cccttccaga gccctccacc cccgcctctg    960
cccagcccac aaggttacca gggcagtttc cactccatcc agagttgctt ccctatggc   1020 gactgctacc ggatggctga accagcagcc ggtggggacg gactggtcgg ggagacccac   1080
ggtttcaacc ccctgcggcc caatggctac cacagcctca gcacgccctt gcctgccaca   1140
ggctatgagg ccctggctga ggcctcatgc cccacagcgc tgccacagca gccatctgaa   1200
gatgtggtgt ccagcggccc cgaggactgt ggcttcttcc ccaatggagc ctttgaccac   1260
tgcctgggcc acatcccctc catctacaca gacacctga                           1299
```

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tggagaaacc tgccaagtat g                                               21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggagacaacc tggtcctcag                                                 20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tttgtcaagc agcaccttg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggtctgaagg tcacctgctc                                                 20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
atgttcgtca tgggtgtgaa                                                 20

```
<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgtggtcatg agtccttcca                                                    20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gccatcaagc agatcactgt                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
caggtgttgg ttcacaaagg                                                    20
```

METHOD FOR PRODUCING PANCREATIC ENDOCRINE CELLS, AND TRANSDIFFERENTIATION AGENT

CROSS-REFERENCE TO RELATED APPLICATIONS

The present application is a U.S. National Phase Application under 35 U.S.C. 371 of International Application No. PCT/JP2016/082095 filed 28 Oct. 2016, which is based on and claims the benefit of priority from Japanese Patent Application No. 2015-212563 filed 29 Oct. 2015, the disclosure of each of which is hereby incorporate by reference in their entireties.

TECHNICAL FIELD

The present invention relates to a method for producing pancreatic endocrine cells from somatic cells and a transdifferentiation agent that transdifferentiates somatic cells to pancreatic endocrine cells.

BACKGROUND ART

Pancreatic endocrine cells have been expected to be used as, for example, a material for regenerative therapies for diabetes or a material used for screening of diabetes drugs. In terms of the regenerative therapies, for example, it has been expected that β cells, which are one of the pancreatic endocrine cells and produce insulin, are administered to type I diabetes patients who are insulin-deficient.

Therefore, keen demand has arisen for developing a method for preparing pancreatic endocrine cells in vitro in large quantities.

There has been proposed a method for producing β cells using embryonic stem cells (hereinafter may be referred to as "ES cells") or induced pluripotent stem cells (hereinafter may be referred to as "iPS cells"). However, the method has the following problems. Firstly, the method is complicated because culturing environments are needed to be properly adjusted by, for example, adding various inhibitors involved in development or differentiation to a cell culture medium. Secondly, the method may be unreproducible. Thirdly, the method is problematic in terms of efficiency because other cells than the β cells are also produced. Finally, the method takes at least 21 days to 30 days to produce the β cells, that is, the β cells are not capable of being produced in a short period of time.

Therefore, at present, keen demand has arisen for promptly providing a method for producing pancreatic endocrine cells, the method being simple, easily reproduced, excellent in production efficiency, and capable of producing the pancreatic endocrine cells in a short period of time.

Note that, GLIS1 (GLIS family zinc finger 1) has been known to improve an establishment improving efficiency of iPS cells (see, e.g., PTL 1).

However, it has not been that the GLIS1 is involved in direct transformation of somatic cells into pancreatic endocrine cells without undergoing the stem cell stage.

CITATION LIST

Patent Literature

PTL 1: Japanese Patent Application Laid-Open (JP-A) No. 2013-519371

SUMMARY OF INVENTION

Technical Problem

The present invention aims to solve the above existing problems and achieve the following object. That is, the present invention has an object to provide a method for producing pancreatic endocrine cells, the method being simple, easily reproduced, excellent in production efficiency, and capable of producing the pancreatic endocrine cells in a short period of time, and a transdifferentiation agent that transdifferentiates somatic cells to pancreatic endocrine cells.

Solution to Problem

Means for solving the above problems are as follows.
<1> A method for producing pancreatic endocrine cells, the method including introducing (A), (B), (C), or (D) below into somatic cells:
(A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof.
(B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof.
(C) a GLIS1 gene or one or more gene products thereof, a Neurogenin3 gene or one or more gene products thereof, a Pdx1 gene or one or more gene products thereof, and a MafA gene or one or more gene products thereof; and
(D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof.
<2> A transdifferentiation agent including
(A), (B), (C), or (D) below:
(A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof.
(B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof.
(C) a GLIS1 gene or one or more gene products thereof, a Neurogenin3 gene or one or more gene products thereof, a Pdx1 gene or one or more gene products thereof, and a MafA gene or one or more gene products thereof; and
(D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof.
wherein the transdifferentiation agent is configured to transdifferentiate somatic cells into pancreatic endocrine cells.

Advantageous Effects of Invention

According to the present invention, it is possible to solve the above existing problems and achieve the above object.

That is, the present invention can provide a method for producing pancreatic endocrine cells, the method being simple, easily reproduced, excellent in production efficiency, and capable of producing the pancreatic endocrine cells in a short period of time and a transdifferentiation agent that transdifferentiates somatic cells to pancreatic endocrine cells.

Figure 1A:
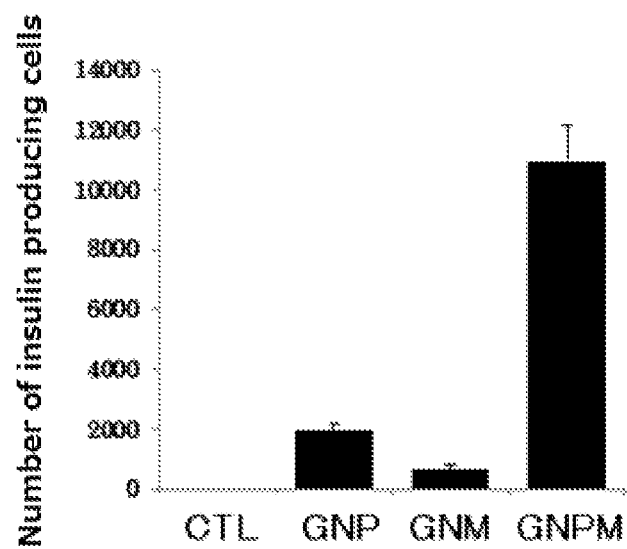
FIG. 1A is a graph illustrating the measurement results of the number of DsRed2-positive insulin producing cells in Test Example 1-1.

DESCRIPTION OF EMBODIMENTS (Production Method of Pancreatic Endocrine Cells)

The method for producing pancreatic endocrine cells of the present invention includes at least an introduction step; and, if necessary, further includes other steps.

<Introduction Step>

The introduction step is a step of introducing (A), (B), (C), or (D) below into somatic cells:

(A) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof (hereinafter may be referred to as "gene or one or more gene products thereof (A)");

(B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof (hereinafter may be referred to as "gene or one or more gene products thereof (B)");

(C) a GLIS1 gene or one or more gene products thereof, a Neurogenin3 gene or one or more gene products thereof, a Pdx1 gene or one or more gene products thereof, and a MafA gene or one or more gene products thereof (hereinafter may be referred to as "gene or one or more gene products thereof (C)"); and (D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof (hereinafter may be referred to as "gene or one or more gene products thereof (D)").

The gene products refer to mRNAs transcribed from genes or proteins translated from the mRNAs.

<<Genes or One or More Gene Products Thereof>>

Aspect

An aspect of the genes or one or more gene products thereof to be introduced into the somatic cells in the introduction step is not particularly limited and may be appropriately selected depending on the intended purpose, so long as the genes or one or more gene products thereof (A), the genes or one or more gene products thereof (B), the genes or one or more gene products thereof (C), or the genes or one or more gene products thereof (D) is included. However, from the viewpoint of excellent production efficiency of the pancreatic endocrine cells, the genes or one or more gene products thereof (A), the genes or one or more gene products thereof (B), or the genes or one or more gene products thereof (D) is preferably included, and the genes or one or more gene products thereof (A) or the genes or one or more gene products thereof (D) is more preferably included.

The genes or one or more gene products thereof to be introduced into the somatic cells in the introduction step may consist of the genes or one or more gene products thereof (A), the gene or one or more gene products thereof (B), the genes or one or more gene products thereof (C), or the genes or one or more gene products thereof (D), or may include other genes or one or more gene products thereof.

GLIS1 Gene or One or More Gene Products Thereof

A source of the GLIS1 gene is not particularly limited and may be appropriately selected depending on the intended purpose. Examples thereof include human and mouse.

Sequence information of the GLIS1 gene is available from known databases. For example, the sequence information is available from NCBI under Accession numbers of NM_147193 (human) or NM_147221 (mouse).

Mutated GLIS1 Gene or One or More Gene Products Thereof

The mutated GLIS1 gene refers to a gene having a sequence identity of 85% or more to a base sequence represented by SEQ ID NO: 1 or 2.

The base sequence represented by SEQ ID NO: 1 refers to a sequence of a gene coding for a protein in which 360 amino acid residues at N-terminus of a mouse GLIS1 protein are deleted.

The base sequence represented by SEQ ID NO: 2 refers to a sequence of a gene coding for a protein in which 190 amino acid residues at N-terminus of a human GLIS1 protein are deleted.

The sequence identity to the base sequence represented by SEQ ID NO: 1 or 2 is not particularly limited and may be appropriately selected depending on the intended purpose, so long as it is 85% or more. However, it is preferably 90% or more, more preferably 95% or more, further preferably 98% or more, particularly preferably 99% or more.

A method for determining the sequence identity is not particularly limited and may be appropriately selected from methods known in the art. For example, the sequence identity can be determined using the algorithm BLAST by Karlin and Altscul (Karlin, S. & Altschul, S. F. (1990) Proc. Natl. Acad. Sci. USA 87: 2264-2268, Karlin, S. & Altschul, S. F., Proc. Natl. Acad. Sci. USA 90: 5873).

Neurogenin3 Gene or One or More Gene Products Thereof

A source of the Neurogenin3 gene is not particularly limited and may be appropriately selected depending on the intended purpose. Examples thereof include human and mouse.

Sequence information of the Neurogenin3 gene is available from known databases. For example, the sequence information is available from NCBI under Accession numbers of NM_009719 (mouse) and NM_020999 (human).

Pdx1 Gene or One or More Gene Products Thereof

A source of the Pdx1 gene is not particularly limited and may be appropriately selected depending on the intended purpose. Examples thereof include human and mouse.

Sequence information of the Pdx1 gene is available from known databases. For example, the sequence information is available from NCBI under Accession numbers of NM_000209 (human) and NM_008814 (mouse).

MafA Gene or One or More Gene Products Thereof

A source of the MafA gene is not particularly limited and may be appropriately selected depending on the intended purpose. Examples thereof include human and mouse.

Sequence information of the MafA gene is available from known databases. For example, the sequence information is available from NCBI under Accession numbers of NM_201589 (human) and NM_194350 (mouse).

Other Genes or One or More Gene Products Thereof

The other genes or one or more gene products thereof are not particularly limited and may be appropriately selected depending on the intended purpose, so long as they do not impair effects of the present invention.

Each of sequences of the GLIS1 gene, the mutated GLIS1 gene, the Neurogenin3 gene, the Pdx1 gene, the MafA gene, and the other genes may consist of a sequence of a protein-coding region in the sequence of each of the genes, or may include other regions than the protein-coding region.

The GLIS1 gene or one or more gene products thereof, the Neurogenin3 gene or one or more gene products thereof, the Pdx1 gene or one or more gene products thereof, the MafA gene or one or more gene products thereof, and the other genes or one or more gene products thereof may have a mutation, so long as they do not impair effects of the present invention.

Examples of the mutation include mutations that do not change an amino acid sequence of a protein from each of the genes and mutations in which one or several (2 to 5) amino acids are deleted, substituted, inserted, or added in an amino acid sequence of a protein from each of the genes.

In the case where the GLIS1 gene or one or more gene products thereof, the Neurogenin3 gene or one or more gene products thereof, the Pdx1 gene or one or more gene products thereof, the MafA gene or one or more gene products thereof, and the other genes or one or more gene products thereof has a mutation, a sequence identity to each of corresponding wild-type genes or one or more gene products thereof is not particularly limited and may be appropriately selected depending on the intended purpose, so long as they do not impair effects of the present invention. However, it is preferably 70% or more, more preferably 80% or more, particularly preferably 90% or more in a base sequence of a region to be translated into a protein.

<<Somatic Cells>>

The somatic cells are not particularly limited and may be appropriately selected depending on the intended purpose. The somatic cells may be undifferentiated precursor cells or terminally differentiated mature cells.

The somatic cells may be derived from ES cells or iPS cells.

Specific examples of the somatic cells include adipose tissue-derived interstitial (stem) cells, neural stem cells, hematopoietic stem cells, mesenchymal stem cells, fibroblasts, hepatic cells, epithelial cells, renal cells, macrophages, lymphocytes, muscle cells, nerve cells, and neuroglia cells. Among them, fibroblasts, mesenchymal stem cells, hepatic cells, epithelial cells, and renal cells are preferable, and fibroblasts and mesenchymal stem cells are more preferable.

A species of an individual from which the somatic cells are harvested is not particularly limited and may be appropriately selected depending on the intended purpose. Examples thereof include human and mouse.

The individual from which the somatic cells are harvested is not particularly limited and may be appropriately selected depending on the intended purpose. In the case where the resultant pancreatic endocrine cells are used for regenerative therapies, the individual is preferably the individual oneself or other individuals having the same or substantially the same MHC type as that of the individual, in terms of a rejection reaction. The phrase "substantially the same MHC type" means, as used herein, that the MHC type is compatible to the extent that, when pancreatic endocrine cells derived from the somatic cells are transplanted into an individual, transplanted cells are capable of being engrafted with the use of, for example, an immunosuppressive agent.

A time when the somatic cells are harvested from the individual is not particularly limited and may be appropriately selected depending on the intended purpose.

A condition under which the somatic cells are cultured is not particularly limited and may be appropriately selected depending on the intended purpose. Examples thereof include a culturing temperature of about 37° C. and a $CO_2$ concentration of from about 2% to about 5%.

A medium in which the somatic cells are cultured is not particularly limited and may be appropriately selected depending on the intended purpose. Examples thereof include minimum essential media (hereinafter may be referred to as "MEM"), Dulbecco's modified Eagle media (hereinafter may be referred to as "DMEM"), RPMI1640 media, 199 media, and F12 media, all of which contain from 5% by mass to 20% by mass of serum.

<<Introduction Method>>

A method for introducing each of the genes or one or more gene products thereof into the somatic cells is not particularly limited and may be appropriately selected depending on the intended purpose. For example, vectors, synthetic mRNA (messenger RNA), or recombinant proteins may be used.

Vector

The vector is not particularly limited and may be appropriately selected depending on the intended purpose. Examples thereof include viral vectors and non-viral vectors.

Specific examples of the viral vectors include retroviral vectors and lentiviral vectors.

Specific examples of the non-viral vectors include plasmid vectors and episomal vectors.

A method for introducing the vector into the somatic cells is not particularly limited and may be appropriately selected from known methods in the art depending on the intended purpose.

In the case where the retroviral vectors are used, the methods described in, for example, WO 2007/69666; Cell, 126, 663-676 (2006); or Cell, 131, 861-872 (2007) may be used. In the case where the lentiviral vectors are used, the methods described in, for example, Science, 318, 1917-1920 (2007) may be used.

In the case where the plasmid vectors are used, the methods described in, for example, Science, 322, 949-953 (2008) may be used. In the case where the episomal vectors are used, the methods described in, for example, Science, 324: 797-801 (2009) or Biochemical and Biophysical Research Communications, 426: 141-147 (2012) may be used.

In the case where the viral vectors are used, viral particles obtained using packaging cells may be used.

The packaging cells are cells into which viral structural protein-coding genes have been introduced. When a recombinant viral vector into which a target gene has been incorporated is introduced into the packaging cells, recombinant viral particles into which the target gene has been incorporated are produced.

The packaging cells are not particularly limited and may be appropriately selected depending on the intended purpose. Examples thereof include packaging cells based on human kidney-derived HEK293 cells or mouse fibroblast-derived NIH3T3 cells; packaging cells Platinum-E (hereinafter may be referred to as "Plat-E cells") which are capable of producing high titer viruses for a long period of time and in which viral structural proteins gag-pol and env are expressed under the control of MoMuLV (Moloney Murine Leukemia Virus) LTR (long terminal repeats); PLAT-A cells that are designed to express Amphotropic virus-derived envelope glycoproteins; and PLAT-GP cells that are designed to express vesicular stomatitis virus-derived envelope glycoproteins.

A method for introducing the viral vector into the packaging cells is not particularly limited and may be appropriately selected depending on the intended purpose. Examples thereof include lipofection methods, electroporation methods, and calcium phosphate methods.

A method for infecting the somatic cells with the resultant viral particles is not particularly limited and may be appropriately selected depending on the intended purpose. Examples thereof include polybrene methods.

The vector may include a marker gene for verifying whether each of the genes has been successfully introduced.

The marker gene refers to a gene that allows for cell sorting or cell selection by introducing the marker gene into a cell. Specific examples of the marker gene include drug resistant genes, fluorescent protein genes, luminescent enzyme genes, and coloring enzyme genes. These may be used alone or in combination.

Specific examples of the drug resistant genes include neomycin resistant genes, tetracycline resistant genes, kanamycin resistant genes, zeocin resistant genes, and hygromycin resistant genes.

Specific examples of the fluorescent protein genes include green fluorescent protein (GFP) genes, yellow fluorescent protein (YFP) genes, and red fluorescent protein (RFP) genes.

Specific examples of the luminescent enzyme gene include luciferase genes.

Specific examples of the coloring enzyme genes include β galactosidase genes, β glucuronidase genes, and alkaline phosphatase genes.

In methods for introducing each of the genes into the somatic cells using the vector, one gene may be incorporated into one vector, or two or more genes may be incorporated into one vector. By incorporating two or more genes into one vector, the two or more genes may be expressed at the same time (hereinafter may be referred to as "co-expression").

A method for incorporating two or more genes into one vector is not particularly limited and may be appropriately selected depending on the intended purpose. However, the two or more genes are preferably incorporated via a linkage sequence.

The linkage sequence is not particularly limited and may be appropriately selected depending on the intended purpose. Examples thereof include gene sequences coding for a foot and mouth disease virus (Picornaviridae Aphthovirus)-derived 2A peptide and IRESs (internal ribosome entry sites).

A method for introducing the mRNA into the somatic cells is not particularly limited and may be appropriately selected from known methods in the art.

A method for introducing the recombinant protein into the somatic cells is not particularly limited and may be appropriately selected from known methods in the art.

The number of times of introduction of each of the genes or one or more gene products thereof into the somatic cells is not particularly limited and may be appropriately selected depending on the intended purpose. For example, each of the genes or one or more gene products thereof may be introduced once or two or more times.

A time when each of the genes or one or more gene products thereof are introduced into the somatic cells is not particularly limited and may be appropriately selected depending on the intended purpose. All the genes or one or more gene products thereof may be introduced at the same time or at different times.

An amount of each of the genes or one or more gene products thereof to be introduced into the somatic cells is not particularly limited and may be appropriately selected depending on the intended purpose. All the genes or one or more gene products thereof may be introduced in an equal amount or different amounts.

For the genes or one or more gene products thereof, genes only, gene products only, or both of genes and gene products in the same gene or one or more gene products thereof may be used.

Moreover, when used in combination with different genes or one or more gene products thereof, the gene or one or more gene products thereof may be a combination of genes only in all the genes or one or more gene products thereof, a combination of gene products only in all the genes or one or more gene products thereof, or a combination of genes in some genes or one or more gene products thereof and gene products in other genes or one or more gene products thereof.

In the introduction step of the genes or one or more gene products thereof, other materials than the genes or one or more gene products thereof may be introduced, so long as they do not impair effects of the present invention.

<<Other Steps>>

The other steps are not particularly limited and may be appropriately selected depending on the intended purpose, so long as they do not impair effects of the present invention. Examples thereof include a genes or genes products thereof-introduced cells culturing step in which somatic cells, into which each of the genes or one or more gene products thereof has been introduced, are cultured.

Genes or Genes Products Thereof-Introduced Cells Culturing Step

The genes or genes products thereof-introduced cells culturing step is a step of culturing somatic cells into which each of the genes or one or more gene products thereof has been introduced.

A condition under which the genes or genes products thereof-introduced cells are cultured is not particularly limited and may be appropriately selected depending on the intended purpose. Examples thereof include a culturing temperature of about 37° C. and a $CO_2$ concentration of from about 2% to about 5%.

A medium used for culturing the genes or genes products thereof-introduced cells is not particularly limited and may be appropriately selected depending on the intended purpose. Examples thereof include MEM, DMEM, RPMI1640 media, 199 media, and F12 media, all of which contain from 5% by mass to 20% by mass of serum.

A period of time for which the genes or genes products thereof-introduced cells are cultured is not particularly limited and may be appropriately selected depending on the intended purpose.

An exchange frequency of the medium is not particularly limited and may be appropriately selected depending on the intended purpose. Examples thereof include every 2 days to 3 days.

<Pancreatic Endocrine Cells>

A method for verifying whether pancreatic endocrine cells are successfully produced by the method for producing pancreatic endocrine cells is not particularly limited and may be appropriately selected depending on the intended purpose. Examples thereof include a method by which expression of proteins to be expressed in the pancreatic endocrine cells is verified and a method by which expression of genes to be expressed in the pancreatic endocrine cells is verified.

For example, whether α cells of the pancreatic endocrine cells are produced is capable of being verified by the presence or absence of glucagon expression, whether β cells of the pancreatic endocrine cells are produced is capable of being verified by the presence or absence of insulin expression, and whether δ cells of the pancreatic endocrine cells are produced is capable of being verified by the presence or absence of somatostatin expression.

The method by which expression of proteins is verified is not particularly limited and may be appropriately selected from known methods in the art. Examples thereof include immunostaining analyses.

The method by which expression of genes is verified is not particularly limited and may be appropriately selected from known methods in the art. Examples thereof include quantitative PCR analyses.

According to the method for producing pancreatic endocrine cells of the present invention, the pancreatic endocrine cells are capable of being produced from somatic cells through transdifferentiation. Therefore, the method is advantageous in that the pancreatic endocrine cells are capable of being produced without undergoing the iPS cell stage that have a risk of forming tumors.

Note that, the transdifferentiation refers to direct transformation from a cell type to another cell type without undergoing the stem cell stage.

The method for producing pancreatic endocrine cells of the present invention is simple and easily reproduced because a gene or one or more gene products thereof only have to be introduced into somatic cells, and at the same time the pancreatic endocrine cells are capable of being produced efficiently in a short period of time. Moreover, the method for producing pancreatic endocrine cells of the present invention is also advantageous in that the pancreatic endocrine cells are capable of being produced without using a special medium for which culturing environments are needed to be properly adjusted, for example, by adding a development inhibitor to the medium.

The pancreatic endocrine cells may be α cells, β cells, δ cells, or mixtures thereof. Among them, β cells are preferable in terms of regenerative therapies for diabetes patients.

The pancreatic endocrine cells of the present invention are suitably available as pancreatic endocrine cells used for, for example, regenerative therapies or screening of diabetes drugs.

(Transdifferentiation Agent)

A transdifferentiation agent of the present invention is a transdifferentiation agent for transdifferentiating somatic cells into pancreatic endocrine cells. The transdifferentiation agent includes at least the gene or one or more gene products thereof (A), the gene or one or more gene products thereof (B), the gene or one or more gene products thereof (C), or the gene or one or more gene products thereof (D); and, if necessary, further includes other components.

<Somatic Cells>

Somatic cells to be targeted by the transdifferentiation agent and preferable aspects thereof are the same as those described under the section entitled "Production method of pancreatic endocrine cells."

<Pancreatic Endocrine Cells>

Pancreatic endocrine cells obtained using the transdifferentiation agent and preferable aspects thereof are the same as those described under the section entitled "Production method of pancreatic endocrine cells."

<Gene or One or More Gene Products Thereof>

Aspect

An aspect of the gene or one or more gene products thereof in the transdifferentiation agent is not particularly limited and may be appropriately selected depending on the intended purpose, so long as so long as the gene or one or more gene products thereof (A), the gene or one or more gene products thereof (B), the gene or one or more gene products thereof (C), or the gene or one or more gene products thereof (D) is included. However, from the viewpoint of excellent production efficiency of the pancreatic endocrine cells, the gene or one or more gene products thereof (A), the gene or one or more gene products thereof (B), or the gene or one or more gene products thereof (D) is preferably included, and the gene or one or more gene products thereof (A) or the gene or one or more gene products thereof (D) is more preferably included.

The gene or one or more gene products thereof in the transdifferentiation agent may consist of the gene or one or more gene products thereof (A), the gene or one or more gene products thereof (B), the gene or one or more gene products thereof (C), or the gene or one or more gene products thereof (D), or may include other genes or one or more gene products thereof.

GLIS1 Gene or One or More Gene Products Thereof

The GLIS1 gene is the same as those described under the section entitled "Production method of pancreatic endocrine cells." The sequence of the GLIS1 gene is also the same as those described under the section entitled "Production method of pancreatic endocrine cells." The GLIS1 gene or one or more gene products thereof may have a mutation which is the same as those described under the section entitled "Production method of pancreatic endocrine cells."

Mutated GLIS1 Gene or One or More Gene Products Thereof

The mutated GLIS1 gene is the same as those described under the section entitled "Production method of pancreatic endocrine cells." The sequence of the mutated GLIS1 gene is also the same as those described under the section entitled "Production method of pancreatic endocrine cells."

Neurogenin3 Gene or One or More Gene Products Thereof

The Neurogenin3 gene is the same as those described under the section entitled "Production method of pancreatic endocrine cells." The sequence of the Neurogenin3 gene is also the same as those described under the section entitled "Production method of pancreatic endocrine cells." The Neurogenin3 gene or one or more gene products thereof may have a mutation which is the same as those described under the section entitled "Production method of pancreatic endocrine cells."

Pdx1 Gene or One or More Gene Products Thereof

The Pdx1 gene is the same as those described under the section entitled "Production method of pancreatic endocrine cells." The sequence of the Pdx1 gene is also the same as those described under the section entitled "Production method of pancreatic endocrine cells." The Pdx1 gene or one or more gene products thereof may have a mutation which is the same as those described under the section entitled "Production method of pancreatic endocrine cells."

MafA Gene or One or More Gene Products Thereof

The MafA gene is the same as those described under the section entitled "Production method of pancreatic endocrine cells." The sequence of the MafA gene is also the same as those described under the section entitled "Production method of pancreatic endocrine cells." The MafA gene or one or more gene products thereof may have a mutation which is the same as those described under the section entitled "Production method of pancreatic endocrine cells."

Other Genes or One or More Gene Products Thereof

The other genes are the same as those described under the section entitled "Production method of pancreatic endocrine cells." The sequences of the other genes are also the same as those described under the section entitled "Production method of pancreatic endocrine cells." The other genes or one or more gene products thereof may have a mutation which is the same as those described under the section entitled "Production method of pancreatic endocrine cells."

Each of the genes or one or more gene products thereof in the transdifferentiation agent may be incorporated into a vector, or may be a synthetic mRNA or a recombinant protein.

The vector may be the same as those described under the section entitled "Production method of pancreatic endocrine cells."

The synthetic mRNA and the recombinant protein may be produced by any of known methods in the art.

<Other Components>

The other components are not particularly limited and may be appropriately selected depending on the intended purpose, so long as they do not impair effects of the present invention.

The genes or one or more gene products thereof in the transdifferentiation agent may be divided into separate containers or may be placed in a single container. Alternatively, any number of the genes or one or more gene products thereof may be placed in each container.

An amount of each of the genes or one or more gene products thereof in the transdifferentiation agent is not particularly limited. All the genes or one or more gene products thereof may be included in an equal amount or different amounts.

The transdifferentiation agent may be suitably used as a component of a kit for producing pancreatic endocrine cells.

The kit for producing pancreatic endocrine cells includes at least the transdifferentiation agent; and, if necessary, further includes other components.

The other components in the kit for producing pancreatic endocrine cells are not particularly limited and may be appropriately selected depending on the intended purpose, so long as they do not impair effects of the present invention. Examples thereof include packaging cells and media.

The packaging cells and the media may be the same as those described under the section entitled "Production method of pancreatic endocrine cells."

EXAMPLES

The present invention will now be described with reference to Test Examples described below, but the present invention is not limited thereto in any way.

Test Example 1-1

Production of Pancreatic Endocrine Cells-1-1

<Preparation of Cells>

Dual-labeled-mouse embryonic fibroblasts (hereinafter may be referred to as "dMEF"), which were a kind of somatic cells, were prepared in the following manner.

Production of Genetically Modified Mice in Which Pancreatic Endocrine Precursor Cells are Fluorescently Labeled with GFP Genetically modified mice in which pancreatic endocrine precursor cells are fluorescently labeled with GFP (mice expressing EGFP under the control of an Ngn3 gene promoter (Ngn3-eGFP)) were produced in the following manner.

A construct, in which a fusion protein gene of GFP and a nuclear localization signal (hereinafter may be referred to as "nls") was ligated downstream of the Ngn3 gene promoter (5 kb) isolated from a BAC clone, was microinjected into about 400 fertilized eggs to thereby produce genetically modified mice in which pancreatic endocrine precursor cells are fluorescently labeled with GFP.

Production of Genetically Modified Mice in Which Pancreatic β Cells are Fluorescently Labeled with DsRed2

Genetically modified mice in which pancreatic β cells are fluorescently labeled with DsRed2 (mice expressing DsRed2 under the control of a rat insulin promoter (Ins-DsR)) were produced in the following manner.

A construct, in which a DsRed2 gene was ligated downstream of the rat insulin promoter (800 bp), was microinjected into about 400 fertilized eggs to thereby produce genetically modified mice in which pancreatic β cells are fluorescently labeled with DsRed2.

Production of Dual-Labeled-Mouse Embryonic Fibroblasts

The genetically modified mice in which pancreatic endocrine precursor cells are fluorescently labeled with GFP were crossed with the genetically modified mice in which pancreatic β cells are fluorescently labeled with DsRed2, and then male and female offspring mice (heterozygous) were crossed with each other to generate dual-labeled genetically modified mice (Ngn3-eGFP/Ins-DsR) that were confirmed to be homozygous by genomic southern blotting. Two pairs (male and female) of the homozygous dual-labeled genetically modified mice were crossed. At embryonic day 14.5, 16 embryos were removed from the uterus by a pair of forceps, and their blood was washed off with 10 mL of phosphate-buffered saline (containing 10 mg/mL kanamycin) in a 10 cm Petri dish within a clean bench. Then, the embryos were minced with a pair of scissors in 10 mL of DMEM (available from Sigma, #D5796; containing penicillin, streptomycin, and 10% FBS) in a 10 cm cell culture dish (available from TPP, #93150). The thus-minced embryonic tissue was transferred into a 15 mL tube and centrifuged at 1.4 krpm at room temperature for 4 min. The supernatant was discarded. The remaining pellet was added with and suspended in 1 mL of a 0.25% trypsin-containing EDTA solution (available from Wako Pure Chemical Industries, Ltd., #201-16945, containing 0.25% DNase I), and then incubated in a water bath at 37° C. The water bath was stirred by hand every 10 min. The minced embryonic tissue corresponding to one animal was well-suspended in 5 mL of DMEM (containing 10% FBS) in a 15 mL tube, transferred into 5 mL of DMEM in a 10 cm cell culture dish, and then incubated within an incubator with 5% $CO_2$ at 37° C. On the following day, the 10 mL DMEM (containing 10% FBS) was replaced with fresh medium and subsequently changed every 2 days. About 4 to about 5 days after, dMEFs in the confluent 10 cm culture dish were washed with 6 mL of phosphate-buffered saline (hereinafter may be referred to as "PBS"). One milliliter of a 0.25% trypsin-containing EDTA solution was added thereto, and incubated within an incubator with 5% $CO_2$ at 37° C. for 2 min. Then, the cells were confirmed to be peeled off. Ten milliliters of DMEM (containing 10% FBS) was added thereto and the cells were well-suspended. The dMEFs for one culture dish were seeded onto new five 10 cm culture dishes and further cultured. After 5 to 6 days of culturing, the dMEFs were confirmed to be grown confluent and washed with 6 mL of PBS. One milliliter of a 0.25% trypsin/EDTA solution was added thereto, and incubated within an incubator with 5% $CO_2$ at 37° C. for 2 min. Then, the cells were confirmed to be peeled off. Six milliliters of DMEM (containing 10% FBS) was added thereto and the cells were well-suspended. The resultant suspension liquid was transferred into a 50 mL tube and centrifuged at 1.4 krpm at room temperature for 4 min. Then, the supernatant was discarded. The remaining cell pellet was added with and suspended in 10 mL of CELLBANKER (available from Takara Bio Inc., #CB011). The resultant suspension liquid was dispensed into vial tubes (0.5 mL per tube) and stored in a deep freezer at −145° C.

<Production of Retrovirus>

Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

Preparation of Plasmid DNA

[pMX-GFP Vector]

A pMX-GFP vector is a vector in which a gene coding for a full-length GFP protein is inserted into a multi-cloning site of a pMX vector and a pMXpuro vector (obtained from The Institute of Medical Science, The University of Tokyo). Note that, the sequence of the gene coding for a full-length GFP protein is deposited in NCBI under Accession number L29345.

[pMX-Mouse GLIS1 Vector]

A pMX-mouse GLIS1 vector is a vector in which a gene coding for a full-length mouse GLIS1 protein is inserted into a multi-cloning site of a pMX vector (available from Addgene). Note that, the sequence of the gene coding for a full-length mouse GLIS1 protein is deposited in NCBI under Accession number NM_147221.

[pMX-Mouse Neurogenin3 Vector]

A pMX-mouse Neurogenin3 vector is a vector in which a gene coding for a full-length mouse Neurogenin3 protein is inserted into a multi-cloning site of a pMX vector (obtained from The Institute of Medical Science, The University of Tokyo). Note that, the sequence of the gene coding for a full-length mouse Neurogenin3 protein is deposited in NCBI under Accession number NM_009719.

[pMX-Mouse Pdx1 Vector]

A pMX-mouse Pdx1 vector is a vector in which a gene coding for a full-length mouse Pdx1 protein is inserted into a multi-cloning site of a pMX vector (obtained from The Institute of Medical Science, The University of Tokyo). Note that, the sequence of the gene coding for a full-length mouse Pdx1 protein is deposited in NCBI under Accession number NM_008814.

[pMX-Mouse MafA Vector]

A pMX-mouse MafA vector is a vector in which a gene coding for a full-length mouse MafA protein is inserted into a multi-cloning site of a pMX vector (obtained from The Institute of Medical Science, The University of Tokyo). Note that, the sequence of the gene coding for a full-length mouse MafA protein is deposited in NCBI under Accession number NM_194350.

Production of Retrovirus

The Plat-E cells were seeded in a 6-well plate (available from TPP, 92406), which had been coated (for 1 hour at 37° C. and 5% $CO_2$) with Poly-L-Lysine (available from Sigma, P8920) diluted 10 fold with PBS, at 8×10$^5$ cells per well, and cultured overnight.

On the following day, 4 µg of the plasmid DNA was placed into a 1.5 mL tube containing 250 µL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 µL of LIPOFECTAMINE (registered trademark) 2000 (LP2000) (available from Life Technologies Corporation, 11668500) was placed into another 1.5 mL tube containing 250 µL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-E cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 μm), 10462100) to thereby remove the Plat-E cells. The culture supernatant containing viral particles were transferred into a 2.0 mL tube.

Thus, a pMX-GFP vector-derived viral solution, a pMX-mouse GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained.

<Introduction>

The dMEFs were infected with the retrovirus to thereby introduce the gene(s) into the cells. The infection was performed in the following manner.

The dMEFs were seeded in a 24-well plate at $2.5 \times 10^4$ cells per well.

On the following day, an 8 mg/mL polybrene solution (available from Sigma, 107689) was added to the viral solution at a final concentration of 8 μg/mL. The culture supernatant of the dMEFs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8μg/mL polybrene.

After the addition of the viral solutions, the resultant solutions were incubated within an incubator with 5% $CO_2$ at 37° C. During the incubation, the media were changed every 2 or 3 days.

[Viral Solution]
(1) pMX-GFP Vector-Derived Viral Solution (Control)
(2) pMX-mouse GLIS1 vector-derived viral solution, pMX-mouse Neurogenin3 vector-derived viral solution, and pMX-mouse Pdx1 vector-derived viral solution
(3) pMX-mouse GLIS1 vector-derived viral solution, pMX-mouse Neurogenin3 vector-derived viral solution, and pMX-mouse MafA vector-derived viral solution
(4) pMX-mouse GLIS1 vector-derived viral solution, pMX-mouse Neurogenin3 vector-derived viral solution, pMX-mouse Pdx1 vector-derived viral solution, and pMX-mouse MafA vector derived viral solution <Determination of Number of dMEF-Derived Insulin Producing Cells>

After the introduction and 22 days of culturing, DsRed2-positive insulin producing cells were photographed by a fluorescence microscope (CARL ZEISS AXIOVERT 200M) unit.

A statistical analysis was performed in the following manner.

HOECHST 33342 (available from Life Technologies Corporation, H1399) was added to wells of a cell culture multi-well plate at a final concentration of 0.1 μg/mL and incubated within an incubator with 5% $CO_2$ at 37° C. for 30 min or longer. Then, images were taken in 100 fields of view for each well using a high-end cell imaging apparatus (available from Thermo Fisher Scientific Inc., ARRAY-SCAN XTI) with a 10× objective lens. The number of the DsRed2-positive insulin producing cells relative to the number of total cells was determined in the 100 fields of view. The results are presented in FIG. 1A.

In FIG. 1A, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, "GNM" represents the result in the case of using the (3) pMX-mouse GLIS1 vector-derived viral solution, pMX-mouse Neurogenin3 vector-derived viral solution, and pMX-mouse MafA vector-derived viral solution, and "GNPM" represents the result in the case of using the (4) pMX-mouse GLIS1 vector-derived viral solution, pMX-mouse Neurogenin3 vector-derived viral solution, pMX-mouse Pdx1 vector derived viral solution, and pMX-mouse MafA vector-derived viral solution.

It was demonstrated from the results of FIG. 1A that production efficiency of the pancreatic endocrine cells was significantly improved in the case where four factors, i.e., the GLIS1, the Neurogenin3, the Pdx1, and the MafA were used, which was one aspect of the method of the present invention.

<Quantitative PCR Analysis>

A quantitative PCR analysis was performed as described below using the cells, which had been subjected to the introduction and cultured for 24 days, to thereby determine a relative expression level of an insulin gene relative to that of a GAPDH gene.

The cells were suspended in a cell lysis solution, and subjected to RNA preparation and cDNA synthesis using SUPERPREP™ Cell Lysis & RT Kit for qPCR (available from TOYOBO CO., LTD., #SCQ-101) or SV 96 Total RNA Isolation System (available from Promega, #Z3505), REVERTRAACE qPCR RT Master Mix with gDNA Remover (available from TOYOBO CO., LTD., #FSQ-301) and then to the quantitative PCR analysis using GENEACE SYBR qPCR Mixα (available from NIPPON GENE CO., LTD.) by means of LIGHT CYCLER 480 (available from Roche).

Note that, the following primers were used for the quantitative PCR analysis.

Mouse GAPDH Gene
  Forward: 5'-tggagaaacctgccaagtatg-3' (SEQ ID NO: 3)
  Reverse: 5'-ggagacaacctggtcctcag-3' (SEQ ID NO: 4)
Mouse Insulin2 Gene
  Forward: 5'-tttgtcaagcagcacctttg-3' (SEQ ID NO: 5)
  Reverse: 5'-ggtctgaaggtcacctgctc-3' (SEQ ID NO: 6)

Figure 1B:
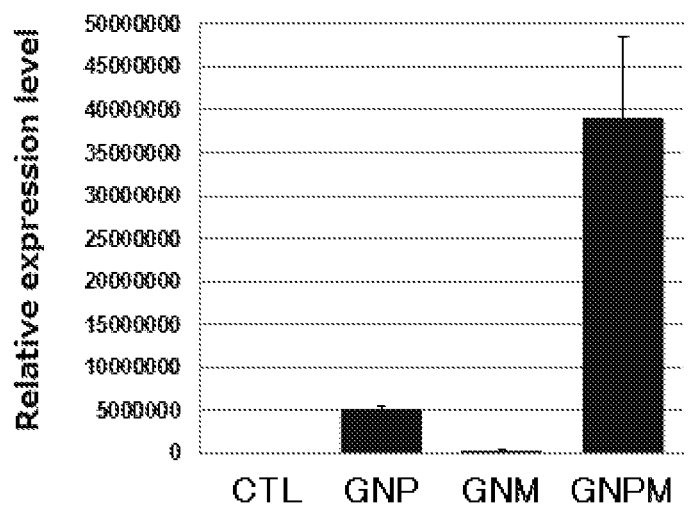
FIG. 1B is a graph illustrating the measurement results of a relative expression level of an insulin gene in Test Example 1-1.

The results of the quantitative PCR analysis are presented in FIG. 1B. In FIG. 1B, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, "GNM" represents the result in the case of using the (3) pMX-mouse GLIS1 vector-derived viral solution, pMX-mouse Neurogenin3 vector-derived viral solution, and pMX-mouse MafA vector-derived viral solution, and "GNPM" represents the result in the case of using the (4) pMX-mouse GLIS1 vector-derived viral solution, pMX-mouse Neurogenin3 vector-derived viral solution, pMX-mouse Pdx1 vector derived viral solution, and pMX-mouse MafA vector-derived viral solution.

It was demonstrated from the results of FIG. 1B that an expression level of the insulin gene was also increased in the case where four factors, i.e., the GLIS1, the Neurogenin3, the Pdx1, and the MafA were used, which was one aspect of the method of the present invention. This also indicates that the production efficiency of the pancreatic endocrine cells was significantly improved.

Test Example 1-2

Production of Pancreatic Endocrine Cells-1-2

<Preparation of Cells>
The dMEFs were prepared in the same manner as in the Test Example 1-1.
<Production of Retrovirus>
Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).
Preparation of Plasmid DNA
[pMX-GFP Vector]
The pMX-GFP vector was prepared in the same manner as in the Test Example 1-1.
[pMX-human GLIS1 Vector]
A pMX-human GLIS1 vector is a vector in which a gene coding for a full-length pMX-human GLIS1 protein is inserted into a multi-cloning site of a pMX vector (available from Addgene). Note that, the sequence of the gene coding for a full-length pMX-human GLIS1 protein is deposited in NCBI under Accession number NM_147193.
[pMX-Human Neurogenin3 Vector]
A pMX-human Neurogenin3 vector is a vector in which a gene coding for a full-length human Neurogenin3 protein is inserted into a multi-cloning site of a pMX vector (obtained from The Institute of Medical Science, The University of Tokyo). Note that, the sequence of the gene coding for a full-length human Neurogenin3 protein is deposited in NCBI under Accession number NM_020999.
[pMX-Human Pdx1 Vector]
A pMX-human Pdx1 vector is a vector in which a gene coding for a full-length human Pdx1 protein is inserted into a multi-cloning site of a pMX vector (obtained from The Institute of Medical Science, The University of Tokyo). Note that, the sequence of the gene coding for a full-length human Pdx1 protein is deposited in NCBI under Accession number NM_000209.
[pMX-Human MafA Vector]
A pMX-human MafA vector is a vector in which a gene coding for a full-length human MafA protein is inserted into a multi-cloning site of a pMX vector (obtained from The Institute of Medical Science, The University of Tokyo). Note that, the sequence of the gene coding for a full-length human MafA protein is deposited in NCBI under Accession number NM_201589.
Production of Retrovirus
The Plat-GP cells were seeded in a 6-well plate (available from TPP, 92406), which had been coated (for 1 hour at 37° C. and 5% $CO_2$) with Poly-L-Lysine (available from Sigma, P8920) diluted 10 fold with PBS, at $8\times10^5$ cells per well, and cultured overnight.
On the following day, 4 μg of the plasmid DNA (2 μg of the pMX vector and 2 μg of the VSVG vector) was placed into a 1.5 mL tube containing 250 μL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 μL of LIPOFECTAMINE (registered trademark) 2000 (LP2000) (available from Life Technologies Corporation, 11668500) was placed into another 1.5 mL tube containing 250 μL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-GP cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 μm), 10462100) to thereby remove the Plat-GP cells. The culture supernatant containing viral particles were transferred into a 2.0 mL tube.

Thus, a pMX-GFP vector-derived viral solution, a pMX-human GLIS1 vector-derived viral solution, a pMX-human Neurogenin3 vector-derived viral solution, a pMX-human Pdx1 vector-derived viral solution, and pMX-human MafA vector-derived viral solution were obtained.
<Introduction>
The dMEFs were infected with the retrovirus to thereby introduce the gene(s) into the cells. The infection was performed in the following manner.

The dMEFs were seeded in a 24-well plate at $2.5\times10^4$ cells per well.

On the following day, an 8 mg/mL polybrene solution (available from Sigma, 107689) was added to the viral solution at a final concentration of 8 μg/mL. The culture supernatant of the dMEFs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8 μg/mL polybrene. After the addition of the viral solutions, the resultant solutions were incubated within an incubator with 5% $CO_2$ at 37° C. During the incubation, the media were changed every 2 or 3 days.
[Viral Solution]
(1) pMX-GFP Vector-Derived Viral Solution (Control)
(2) pMX-human GLIS1 vector-derived viral solution, pMX-human Neurogenin3 vector-derived viral solution, and pMX-human Pdx1 vector-derived viral solution
(3) pMX-human GLIS1 vector-derived viral solution, pMX-human Neurogenin3 vector-derived viral solution, and pMX-human MafA vector-derived viral solution
(4) pMX-human GLIS1 vector-derived viral solution, pMX-human Neurogenin3 vector-derived viral solution, pMX-human Pdx1 vector-derived viral solution, and pMX-human MafA vector-derived viral solution
<Quantitative PCR Analysis>
The quantitative PCR analysis was performed in the same manner as in the Test Example 1-1.

Figure 1C:
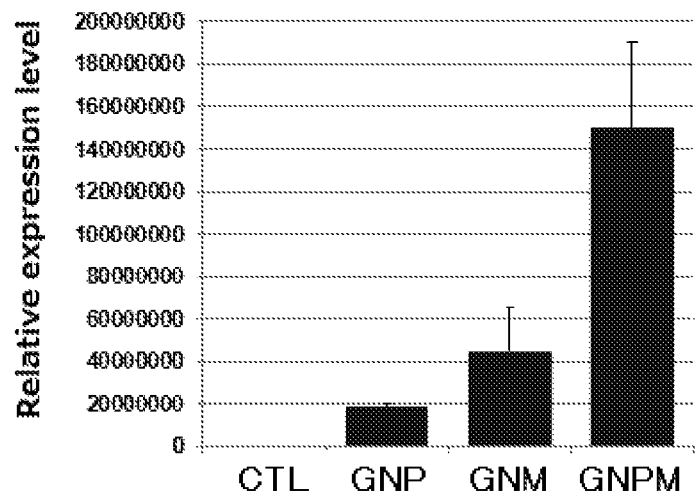
FIG. 1C is a graph illustrating the measurement results of a relative expression level of an insulin gene in Test Example 1-2.

The results of the quantitative PCR analysis are presented in FIG. 1C. In FIG. 1C, "CTL" represents the result in the case of using the (1) pMX-GFP vector-derived viral solution (control), "GNP" represents the result in the case of using the (2) pMX-human GLIS1 vector-derived viral solution, pMX-human Neurogenin3 vector-derived viral solution, and pMX-human Pdx1 vector-derived viral solution, "GNM" represents the result in the case of using the (3) pMX-human GLIS1 vector-derived viral solution, pMX-human Neurogenin3 vector-derived viral solution, and pMX-human MafA vector derived viral solution, and "GNPM" represents the result in the case of using the (4) pMX-human GLIS1 vector-derived viral solution, pMX-human Neurogenin3 vector-derived viral solution, pMX-human Pdx1 vector-derived viral solution, and pMX-human MafA vector-derived viral solution.

It was demonstrated from the results of FIG. 1C that, when human genes were used, the expression level of the insulin gene was similarly increased and thus the production efficiency of the pancreatic endocrine cells was significantly improved in the case where four factors, i.e., the GLIS1, the Neurogenin3, the Pdx1, and the MafA were used, which was one aspect of the method of the present invention.

Test Example 2-1

Production of Pancreatic Endocrine Cells-2-1

<Preparation of Cells>
The dMEFs were prepared in the same manner as in the Test Example 1-1.
<Production of Retrovirus>
The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).
Preparation of Plasmid DNA
[pMX-GFP Vector]
The pMX-GFP vector was prepared in the same manner as in the Test Example 1-1.
[pMX-Mouse GLIS1 Vector]
The pMX-mouse GLIS1 vector was prepared in the same manner as in the Test Example 1-1.
[pMX-Mouse Mutated GLIS1 Vector]
A pMX-mouse mutated GLIS1 vector is a vector in which a gene coding for a protein in which 360 amino acid residues at N-terminus of a mouse GLIS1 protein are deleted is inserted into a multi-cloning site of a pMX vector (available from Addgene).

A sequence of the gene coding for a protein in which 360 amino acid residues at N-terminus of a mouse GLIS1 protein are deleted is represented by SEQ ID NO: 1 and was prepared in the following manner.

A DNA fragment encoding the protein in which 360 amino acid residues at N-terminus of a mouse GLIS1 protein are deleted was amplified by a PCR method using the pMX-mouse GLIS1 vector as a template DNA and PRIME-STAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.
[pMX-Mouse Neurogenin3 Vector]
The pMX-mouse Neurogenin3 vector was prepared in the same manner as in the Test Example 1-1.

[pMX-Mouse Pdx1 Vector]
The pMX-mouse Pdx1 vector was prepared in the same manner as in the Test Example 1-1.
Production of Retrovirus
A pMX-GFP vector-derived viral solution, a pMX-mouse GLIS1 vector-derived viral solution, a pMX-mouse mutated GLIS1 vector-derived viral solution, a pMX-mouse Neurogenin3 vector-derived viral solution, and a pMX-mouse Pdx1 vector-derived viral solution were obtained in the same manner as in the Test Example 1-1, except that the plasmid DNAs used in the Test Example 1-1 were changed to plasmid DNAs for this Test Example.
<Introduction>
The gene was introduced into the cells in the same manner as in the Test Example 1-1, except that the viral solutions used in the Test Example 1-1 were changed to the following viral solutions.
[Viral Solution]
(1) pMX-GFP vector-derived viral solution (control)
(2) pMX-mouse GLIS1 vector-derived viral solution, pMX-mouse Neurogenin3 vector-derived viral solution, and pMX-mouse Pdx1 vector-derived viral solution
(3) pMX-mouse mutated GLIS1 vector-derived viral solution, pMX-mouse Neurogenin3 vector-derived viral solution, and pMX-mouse Pdx1 vector-derived viral solution
<Determination of Number of dMEF-Derived Insulin Producing Cells>
The number of the DsRed2-positive insulin producing cells was counted in the same manner as in the Test Example 1-1, except that, after the introduction and 17 days of culturing, the DsRed2-positive insulin producing cells were photographed by a fluorescence microscope unit. The results are presented in FIG. 2A.

Figure 2A:
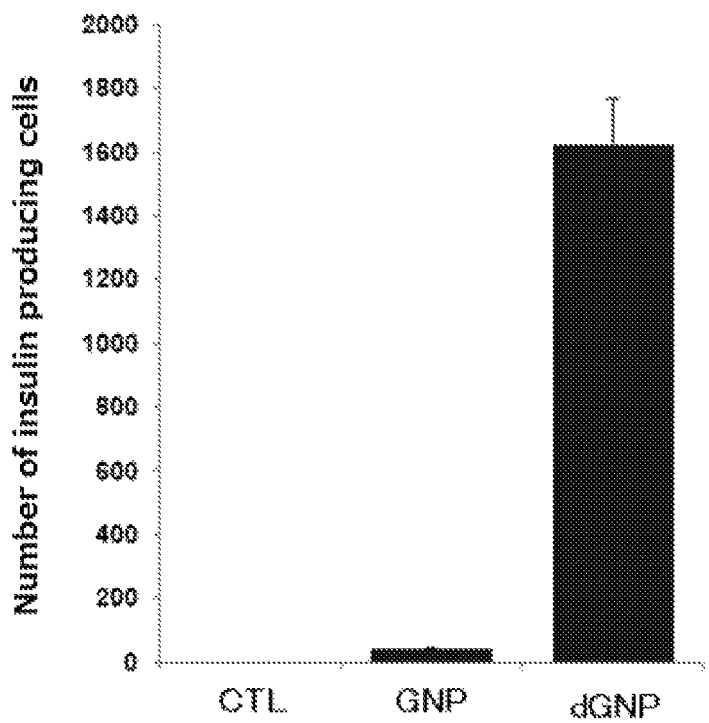
FIG. 2A is a graph illustrating the measurement results of the number of DsRed2-positive insulin producing cells in Test Example 2-1.

In FIG. 2A, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, and "dGNP" represents the result in the case of using the (3) pMX-mouse mutated GLIS1 vector-derived viral solution, pMX-mouse Neurogenin3 vector-derived viral solution, and pMX-mouse Pdx1 vector-derived viral solution.

It was demonstrated from the results of FIG. 2A that the production efficiency of the pancreatic endocrine cells was more significantly improved in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used.
<Quantitative PCR Analysis>
The quantitative PCR analysis was performed in the same manner as in the Test Example 1-1.

Figure 2B:
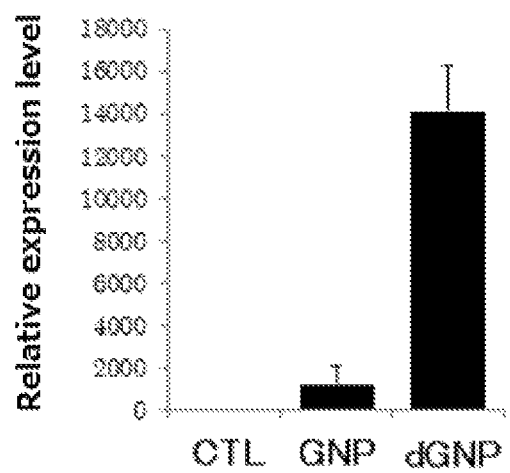
FIG. 2B is a graph illustrating the measurement results of a relative expression level of an insulin gene in Test Example 2-1.

The results are presented in FIG. 2B. In FIG. 2B, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, and "dGNP" represents the result in the case of using the (3) pMX-mouse mutated GLIS1 vector-derived viral solution, pMX-mouse Neurogenin3 vector-derived viral solution, and pMX-mouse Pdx1 vector-derived viral solution.

It was demonstrated from the results of FIG. 2B that the expression level of the insulin gene was also increased in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used. This also indicates that the production efficiency of the pancreatic endocrine cells was significantly improved.

Test Example 2-2

Production of Pancreatic Endocrine Cells-2-2

<Preparation of Cells>

The dMEFs were prepared in the same manner as in the Test Example 1-1.

<Production of Retrovirus>

The Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

Preparation of Plasmid DNA

[pMX-GFP Vector]

The pMX-GFP vector was prepared in the same manner as in the Test Example 1-1.

[pMX-Human GLIS1 Vector]

The pMX-human GLIS1 vector was prepared in the same manner as in the Test Example 1-2.

[pMX-Human Mutated GLIS1 Vector]

A pMX-human mutated GLIS1 vector is a vector in which a gene coding for a protein in which 190 amino acid residues at N-terminus of a human GLIS1 protein are deleted is inserted into a multi-cloning site of a pMX vector (available from Addgene).

A sequence of the gene coding for a protein in which 190 amino acid residues at N-terminus of a human GLIS1 protein are deleted is represented by SEQ ID NO: 2 and was prepared in the following manner.

A DNA fragment encoding the protein in which 190 amino acid residues at N-terminus of a human GLIS1 protein are deleted was amplified by a PCR method using the pMX-human GLIS1 vector as a template DNA and PRIME-STAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Human Neurogenin3 Vector]

The pMX-human Neurogenin3 vector was prepared in the same manner as in the Test Example 1-2.

[pMX-Human Pdx1 Vector]

The pMX-human Pdx1 vector was prepared in the same manner as in the Test Example 1-2.

Production of Retrovirus

A pMX-GFP vector-derived viral solution, a pMX-human GLIS1 vector-derived viral solution, a pMX-human mutated GLIS1 vector-derived viral solution, a pMX-human Neurogenin3 vector-derived viral solution, and a pMX-human Pdx1 vector-derived viral solution were obtained in the same manner as in the Test Example 1-2, except that the plasmid DNAs used in the Test Example 1-2 were changed to plasmid DNAs for this Test Example.

<Introduction>

The gene was introduced into the cells in the same manner as in the Test Example 1-2, except that the viral solutions used in the Test Example 1-2 were changed to the following viral solutions.

[Viral Solution]

(1) pMX-GFP vector-derived viral solution (control)

(2) pMX-human GLIS1 vector-derived viral solution, pMX-human Neurogenin3 vector-derived viral solution, and pMX-human Pdx1 vector-derived viral solution (3) pMX-human mutated GLIS1 vector-derived viral solution, pMX-human Neurogenin3 vector-derived viral solution, and pMX-human Pdx1 vector-derived viral solution <Quantitative PCR Analysis>

The quantitative PCR analysis was performed in the same manner as in the Test Example 1-1.

Figure 2C:
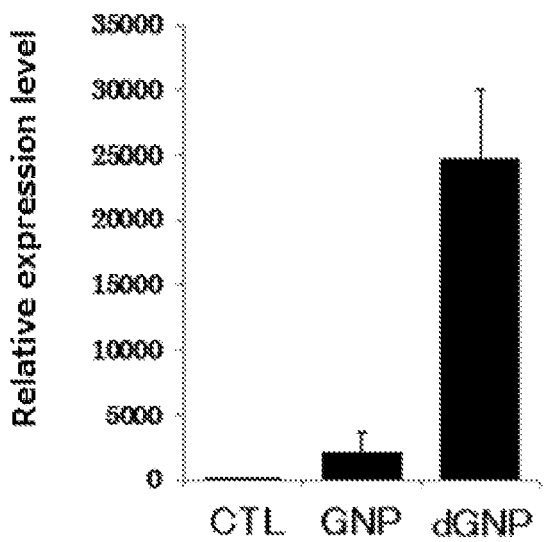
FIG. 2C is a graph illustrating the measurement results of a relative expression level of an insulin gene in Test Example 2-2.

The results are presented in FIG. 2C. In FIG. 2C, "CTL" represents the result in the case of using the (1) pMX-GFP vector-derived viral solution (control), "GNP" represents the result in the case of using the (2) pMX-human GLIS1 vector-derived viral solution, pMX-human Neurogenin3 vector-derived viral solution, and pMX-human Pdx1 vector-derived viral solution, and "dGNP" represents the result in the case of using the (3) pMX-human mutated GLIS1 vector-derived viral solution, pMX-human Neurogenin3 vector-derived viral solution, and pMX-human Pdx1 vector-derived viral solution.

It was demonstrated from the results of FIG. 2C that, when human genes were used, the expression level of the insulin gene was similarly more increased and thus the production efficiency of the pancreatic endocrine cells was more significantly improved in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used.

Test Example 3-1

Production of Pancreatic Endocrine Cells-3-1

<Preparation of Cells>

The dMEFs were prepared in the same manner as in the Test Example 1-1.

<Production of Retrovirus>

The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

Preparation of Plasmid DNA

[pMX-GFP Vector]

The pMX-GFP vector was prepared in the same manner as in the Test Example 1-1.

[pMX-Mouse GLIS1 Vector]

The pMX-mouse GLIS1 vector was prepared in the same manner as in the Test Example 1-1.

[pMX-Mouse Mutated GLIS1 Vector]

The pMX-mouse mutated GLIS1 vector was prepared in the same manner as in the Test Example 2-1.

[pMX-Mouse Neurogenin3 Vector]

The pMX-mouse Neurogenin3 vector was prepared in the same manner as in the Test Example 1-1.

[pMX-Mouse Pdx1 Vector]

The pMX-mouse Pdx1 vector was prepared in the same manner as in the Test Example 1-1.

[pMX-Mouse MafA Vector]

The pMX-mouse MafA vector was prepared in the same manner as in the Test Example 1-1.

Production of Retrovirus

A pMX-GFP vector-derived viral solution, a pMX-mouse GLIS1 vector-derived viral solution, a pMX-mouse mutated GLIS1 vector-derived viral solution, a pMX-mouse Neurogenin3 vector-derived viral solution, a pMX-mouse Pdx1 vector derived viral solution, and a pMX-mouse MafA vector-derived viral solution were obtained in the same manner as in the Test Example 1-1, except that the plasmid DNAs used in the Test Example 1-1 were changed to plasmid DNAs for this Test Example.

<Introduction>

The gene was introduced into the cells in the same manner as in the Test Example 1-1, except that the viral solutions used in the Test Example 1-1 were changed to the following viral solutions.

[Viral Solution]

(1) pMX-GFP vector-derived viral solution (control)
(2) pMX-mouse GLIS1 vector-derived viral solution, pMX-mouse Neurogenin3 vector-derived viral solution, pMX-mouse Pdx1 vector-derived viral solution, and pMX-mouse MafA vector derived viral solution
(3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution <Determination of Number of dMEF-Derived Insulin Producing Cells>

The number of the DsRed2-positive insulin producing cells was counted in the same manner as in the Test Example 1-1, except that, after the introduction and 21 days of culturing, the DsRed2-positive insulin producing cells were photographed by a fluorescence microscope unit. The results are presented in FIG. 3A.

Figure 3A:
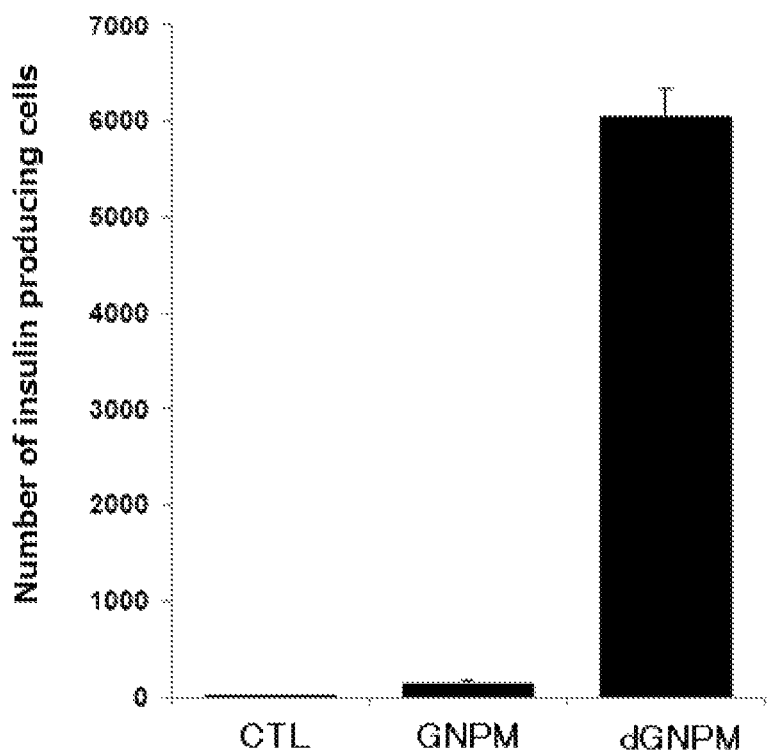
FIG. 3A is a graph illustrating the measurement results of the number of DsRed2-positive insulin producing cells in Test Example 3-1.

In FIG. 3A, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, and "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 3A that the production efficiency of the pancreatic endocrine cells was more significantly improved in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention.

<Quantitative PCR Analysis>

The quantitative PCR analysis was performed in the same manner as in the Test Example 1-1.

Figure 3B:
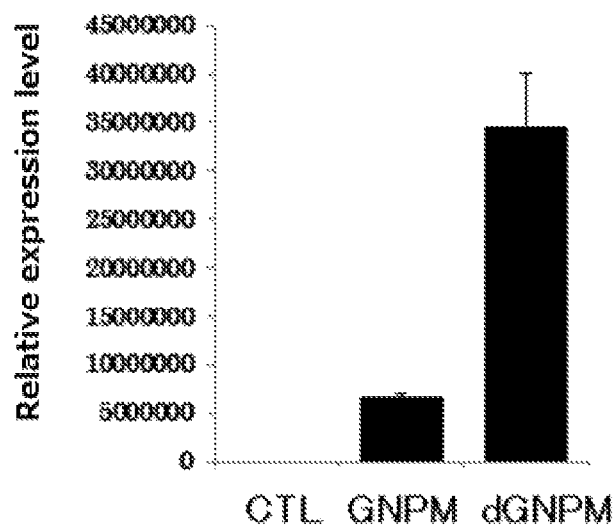
FIG. 3B is a graph illustrating the measurement results of a relative expression level of an insulin gene in Test Example 3-1.

The results are presented in FIG. 3B. In FIG. 3B, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, and "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 3B that the expression level of the insulin gene was also increased in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention. This also indicates that production efficiency of the pancreatic endocrine cells was more significantly improved.

Test Example 3-2

Production of Pancreatic Endocrine Cells-3-2

<Preparation of Cells>

The dMEFs were prepared in the same manner as in the Test Example 1-1.

<Production of Retrovirus>

The Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

Preparation of Plasmid DNA

[pMX-GFP Vector]

The pMX-GFP vector was prepared in the same manner as in the Test Example 1-1.

[pMX-Human GLIS1 Vector]

The pMX-human GLIS1 vector was prepared in the same manner as in the Test Example 1-2.

[pMX-Human Mutated GLIS1 Vector]

The pMX-human mutated GLIS1 vector was prepared in the same manner as in the Test Example 2-2.

[pMX-Human Neurogenin3 Vector]

The pMX-human Neurogenin3 vector was prepared in the same manner as in the Test Example 1-2.

[pMX-Human Pdx1 Vector]

The pMX-human Pdx1 vector was prepared in the same manner as in the Test Example 1-2.

[pMX-Human MafA Vector]

The pMX-human MafA vector was prepared in the same manner as in the Test Example 1-2.

Production of Retrovirus

A pMX-GFP vector-derived viral solution, a pMX-human GLIS1 vector-derived viral solution, a pMX-human mutated GLIS1 vector-derived viral solution, a pMX-human Neurogenin3 vector-derived viral solution, a pMX-human Pdx1 vector-derived viral solution, and a pMX-human MafA vector-derived viral solution were obtained in the same manner as in the Test Example 1-2, except that the plasmid DNAs used in the Test Example 1-2 were changed to plasmid DNAs for this Test Example.

<Introduction>

The gene was introduced into the cells in the same manner as in the Test Example 1-2, except that the viral solutions used in the Test Example 1-2 were changed to the following viral solutions.

[Viral Solution]
(1) pMX-GFP vector-derived viral solution (control)
(2) pMX-human GLIS1 vector-derived viral solution, pMX-human Neurogenin3 vector-derived viral solution, pMX-human Pdx1 vector-derived viral solution, and pMX-human MafA vector-derived viral solution
(3) pMX-human mutated GLIS1 vector-derived viral solution, pMX-human Neurogenin3 vector-derived viral solution, pMX-human Pdx1 vector-derived viral solution, and pMX-human MafA vector-derived viral solution
<Quantitative PCR Analysis>

The quantitative PCR analysis was performed in the same manner as in the Test Example 1-1.

Figure 3C:
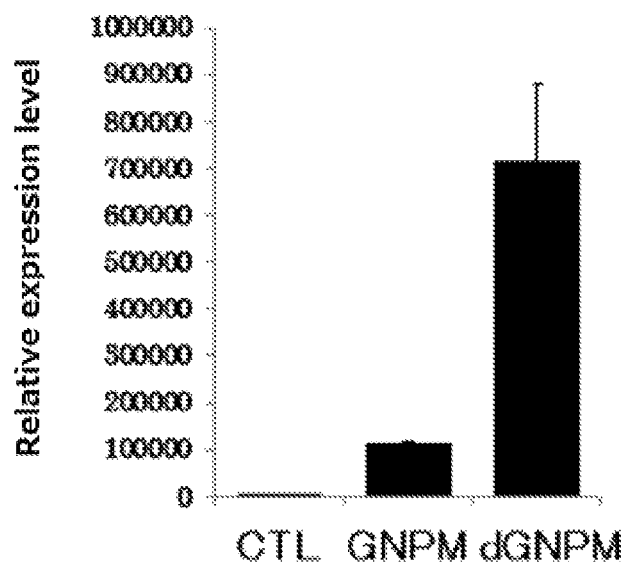
FIG. 3C is a graph illustrating the measurement results of a relative expression level of an insulin gene in Test Example 3-2.

The results are presented in FIG. 3C. In FIG. 3C, "CTL" represents the result in the case of using the (1) pMX-GFP vector-derived viral solution (control), "GNPM" represents the result in the case of using the (2) pMX-human GLIS1 vector-derived viral solution, pMX-human Neurogenin3 vector-derived viral solution, pMX-human Pdx1 vector-derived viral solution, and pMX-human MafA vector-derived viral solution, and "dGNPM" represents the result in the case of using the (3) pMX-human mutated GLIS1 vector-derived viral solution, pMX-human Neurogenin3 vector-derived viral solution, pMX-human Pdx1 vector-derived viral solution, and pMX-human MafA vector-derived viral solution.

It was demonstrated from the results of FIG. 3C that, when human genes were used, the expression level of the insulin gene was similarly more increased and thus the production efficiency of the pancreatic endocrine cells was more significantly improved in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention.

Test Example 4

Glucose-Responsive Insulin Secretion Test-1

<Preparation of Cells>

The dMEFs were prepared in the same manner as in the Test Example 1-1.
<Production of Retrovirus>

The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).
Preparation of Plasmid DNA
[pMX-Mouse GLIS1 Vector]

The pMX-mouse GLIS1 vector was prepared in the same manner as in the Test Example 1-1.
[pMX-Mouse Neurogenin3 Vector]

The pMX-mouse Neurogenin3 vector was prepared in the same manner as in the Test Example 1-1.
[pMX-mouse Pdx1 Vector]

The pMX-mouse Pdx1 vector was prepared in the same manner as in the Test Example 1-1.
[pMX-Mouse MafA Vector]

The pMX-mouse MafA vector was prepared in the same manner as in the Test Example 1-1.

Production of Retrovirus

A pMX-mouse GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained in the same manner as in the Test Example 1-1, except that the plasmid DNAs used in the Test Example 1-1 were changed to plasmid DNAs for this Test Example.
<Introduction>

The gene was introduced into the cells in the same manner as in the Test Example 1-1, except that the viral solutions used in the Test Example 1-1 were changed to the following viral solution.
[Viral Solution]
(1) pMX-mouse GLIS1 vector-derived viral solution, pMX-mouse Neurogenin3 vector-derived viral solution, pMX-mouse Pdx1 vector-derived viral solution, and pMX-mouse MafA vector derived viral solution
<Glucose-Responsive Insulin Secretion Test>

Thirty-four days after the introduction, all of pancreatic islet-like masses were picked up by a pipette and transferred into a 24-well plate (low adhesive plate (EZ-BINDSHUT II, available from AGC TECHNO GLASS CO., LTD.)). Then, a glucose-responsive insulin secretion test was performed in the following manner.

The pancreatic islet-like masses were cultured in a 1.4 mM glucose-containing Ringer's solution for 3 hours. Then, the medium was replaced and the masses were cultured in a 2.8 mM glucose-containing Ringer's solution for another 1 hour, of which culture supernatant was used as a reference (hereinafter may be referred to as "reference culture supernatant").

Then, the pancreatic islet-like masses were cultured in a 16.8 mM glucose-containing Ringer's solution for 1 hour. A culture supernatant thereof was transferred into a 1.5 mL tube (hereinafter may be referred to as "high-glucose culture supernatant").

An insulin concentration in each of the culture supernatants was measured by ELISA assay (human insulin ELISA kit, available from Mercodia). The results are presented in FIG. 4.

Figure 4:
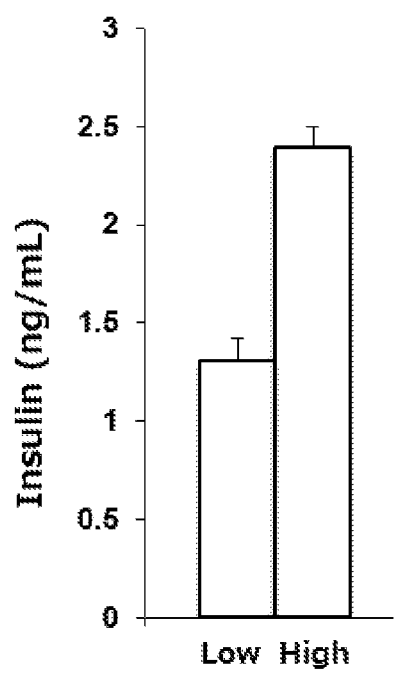
FIG. 4 is a graph illustrating the results of a glucose-responsive insulin secretion test in Test Example 4.

In FIG. 4, a left bar ("low") represents the result of the reference culture supernatant and a right bar ("high") represents the result of the high-glucose culture supernatant.

For the results of FIG. 4, an amount of insulin was small at a low glucose concentration and the amount of insulin was increased at a higher glucose concentration. Therefore, the pancreatic islet-like masses produced by the method of the present invention were confirmed to have functions required for pancreatic endocrine cells.

Test Example 5

Glucose-Responsive Insulin Secretion Test-2

<Preparation of Cells>

The dMEFs were prepared in the same manner as in the Test Example 1-1.
<Production of Retrovirus>

The pMX-mouse GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 4.
<Introduction>

The gene was introduced into the cells in the same manner as in the Test Example 4 using the following viral solution.

[Viral Solution]
(1) pMX-mouse GLIS1 vector-derived viral solution, pMX-mouse Neurogenin3 vector-derived viral solution, pMX-mouse Pdx1 vector-derived viral solution, and pMX-mouse MafA vector derived viral solution <Glucose-Responsive Insulin Secretion Test>

Twenty-seven days after the introduction, 30 uniform pancreatic islet-like masses having a diameter of 100 μm to 300 μm were picked up by a pipette under a stereoscopic microscope and transferred into a 24-well plate (low adhesive plate (EZ-BINDSHUT II, available from AGC TECHNO GLASS CO., LTD.). Then, a glucose-responsive insulin secretion test was performed in the same manner.

The pancreatic islet-like masses were cultured in a 2.8 mM glucose-containing Ringer's solution for 3 hours. Then, the medium was replaced and the masses were cultured for another 1 hour, of which culture supernatant was used as a reference (hereinafter may be referred to as "reference culture supernatant").

Then, the pancreatic islet-like masses were cultured in a 16.8 mM glucose-containing Ringer's solution for 1 hour. A culture supernatant thereof was transferred into a 1.5 mL tube (hereinafter may be referred to as "high-glucose culture supernatant").

Then, a 2.8 mM glucose-containing Ringer's solution was added to wells, where the pancreatic islet-like masses were cultured for 1 hour. A culture supernatant thereof was transferred into a 1.5 mL tube (hereinafter may be referred to as "low-glucose culture supernatant").

An insulin concentration in each of the culture supernatants was measured by ELISA assay (available from Shibayagi Co., Ltd., TYPE T). The results are presented in FIG. 5.

Figure 5:
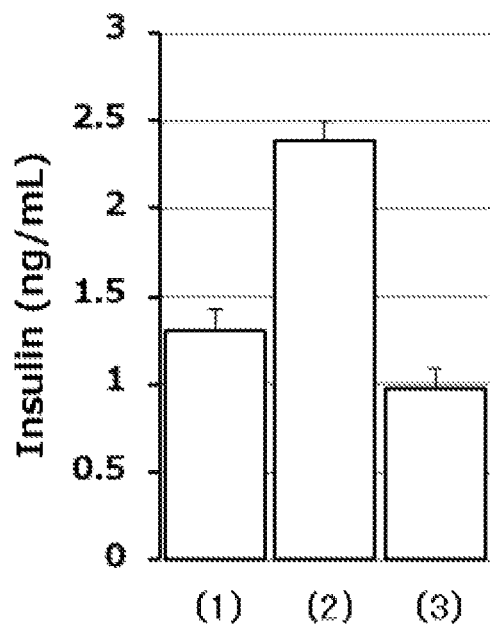
FIG. 5 is a graph illustrating the results of a glucose-responsive insulin secretion test in Test Example 5.

In FIG. 5, a left bar ((1)) represents the result of the reference culture supernatant, a middle bar ((2)) represents the result of the high-glucose culture supernatant, and a right bar ((3)) represents the result of the low-glucose culture supernatant.

It was confirmed from the results of FIG. 5 that an amount of insulin was small at a low glucose concentration ((1)), the amount of insulin was increased at a higher glucose concentration ((2)), and a concentration of insulin was decreased at a lower glucose concentration ((3)). Therefore, also in this Test Example, the pancreatic endocrine cells obtained by the method of the present invention were confirmed to have functions required for pancreatic endocrine cells.

Test Example 6

Production of Pancreatic Endocrine Cells from Mouse Mesenchymal Stem Cells

<Preparation of Cells>

Mouse mesenchymal stem cells (Cyagen catalog No. MUBMX-01001) (hereinafter may be referred to as "mouse MSC") were prepared as cells. The mouse MSCs were subcultured in an ADSC-BM medium (supplemented with 10% FBS, penicillin-streptomycin).

<Production of Retrovirus>

The pMX-GFP vector-derived viral solution, the pMX-mouse GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1.

<Introduction>

The mouse MSCs were infected with the retrovirus to thereby introduce the gene(s) into the cells. The infection was performed in the following manner.

The mouse MSCs were seeded in a 24-well plate at $2.5 \times 10^4$ cells per well.

On the following day, an 8 mg/mL polybrene solution (available from Sigma, 107689) was added to the viral solution at a final concentration of 8 μg/mL. The culture supernatant of the mouse MSCs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8 μg/mL polybrene. After the addition of the viral solutions, the resultant solutions were incubated within an incubator with 5% $CO_2$ at 37° C. During the incubation, the media were changed every 2 or 3 days.

[Viral Solution]
(1) pMX-GFP vector-derived viral solution (control)
(2) pMX-mouse GLIS1 vector-derived viral solution, pMX-mouse Neurogenin3 vector-derived viral solution, pMX-mouse Pdx1 vector-derived viral solution, and pMX-mouse MafA vector derived viral solution <Quantitative PCR Analysis>

The quantitative PCR analysis was performed in the same manner as in the Test Example 1-1.

Figure 6:
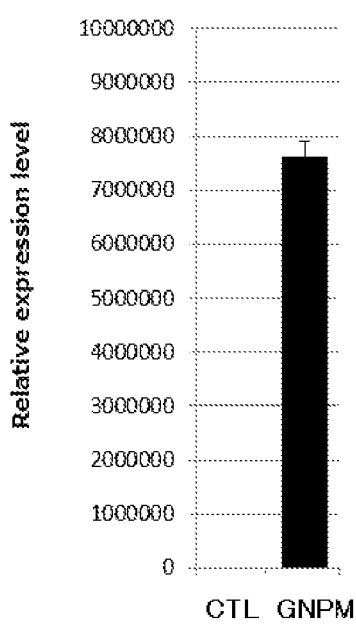
FIG. 6 is a graph illustrating the measurement results of a relative expression level of an insulin gene in Test Example 6.

The results are presented in FIG. 6. In FIG. 6, "CTL" represents the result in the case of using the (1) pMX-GFP vector-derived viral solution (control) and "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 6 that, when the mesenchymal stem cells were used as cells, the pancreatic endocrine cells were similarly able to be produced efficiently by using four factors, i.e., the GLIS1, the Neurogenin3, the Pdx1, and the MafA, which was one aspect of the method of the present invention.

Test Example 7

Production of Pancreatic Endocrine Cells from Human Neonatal Fibroblasts)

<Preparation of Cells>

Human neonatal fibroblasts (NHDF) (D10051, available from TAKARA SHUZO CO., LTD.) were prepared as human cells.

<Production of Retrovirus>

The pMX-GFP vector-derived viral solution, the pMX-human mutated GLIS1 vector-derived viral solution, the pMX-human Neurogenin3 vector-derived viral solution, and the pMX-human MafA vector-derived viral solution were obtained in the same manner as in the Test Example 1-2 or 2-2.

<Introduction>

The genes were introduced into cells in the same manner as in the Test Example 1-2, except that the cells used in the Test Example 1-2 (dMEFs) were changed to the human neonatal fibroblasts. Note that, the following viral solutions were used.

[Viral Solution]
(1) pMX-GFP vector-derived viral solution (control)
(2) pMX-human mutated GLIS1 vector-derived viral solution, pMX-human Neurogenin3 vector-derived viral solution, and pMX-human MafA vector-derived viral solution
<Quantitative PCR Analysis>

The quantitative PCR analysis was performed in the same manner as in the Test Example 1-1, except that the primers used in the Test Example 1-1 were changed to the following primers.
Human GAPDH Gene
    Forward: 5'-atgttcgtcatgggtgtgaa-3' (SEQ ID NO: 7)
    Reverse: 5'- tgtggtcatgagtccttcca-3' (SEQ ID NO: 8)
Human Insulin Gene
    Forward: 5'-gccatcaagcagatcactgt-3' (SEQ ID NO: 9)
    Reverse: 5'-caggtgttggttcacaaagg-3' (SEQ ID NO: 10)

Figure 7:
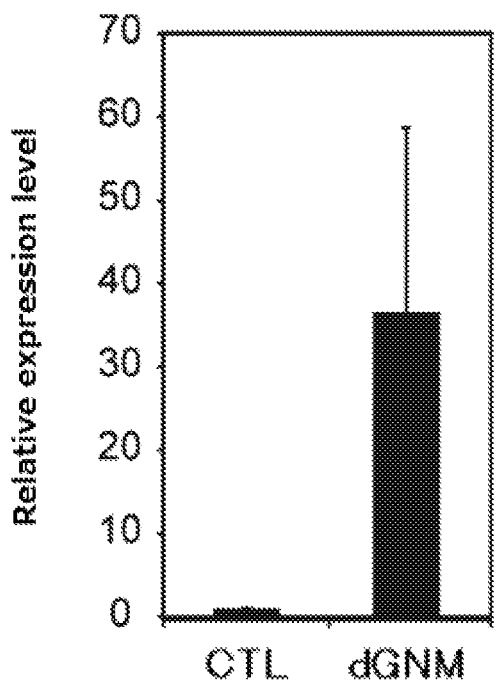
FIG. 7 is a graph illustrating the measurement results of a relative expression level of an insulin gene in Test Example 7.

The results are presented in FIG. 7. In FIG. 7, "CTL" represents the result in the case of using the (1) pMX-GFP vector-derived viral solution (control) and "dGNM" represents the result in the case of using the (2) pMX-human mutated GLIS1 vector-derived viral solution, pMX-human Neurogenin3 vector-derived viral solution, and pMX-human MafA vector-derived viral solution.

It was demonstrated from the results of FIG. 7 that, when human genes were used, the pancreatic endocrine cells were similarly able to be produced efficiently in the case where three factors, i.e., the mutated GLIS1, the Neurogenin3, and the MafA were used, which was one aspect of the method of the present invention.

Test Example 8

Production of Pancreatic Endocrine Cells from Human Glioma T98G Cell Line)

<Preparation of Cells>
Human glioma T98G cell line (RCB1954, RIKEN) were prepared as human cells.
<Production of Retrovirus>
The pMX-GFP vector-derived viral solution, the pMX-human GLIS1 vector-derived viral solution, the pMX-human mutated GLIS1 vector-derived viral solution, the pMX-human Neurogenin3 vector-derived viral solution, the pMX-human Pdx1 vector-derived viral solution, and the pMX-human MafA vector-derived viral solution were obtained in the same manner as in the Test Example 1-2 or 2-2.
<Introduction>
The genes were introduced into cells in the same manner as in the Test Example 1-2, except that the cells used in the Test Example 1-2 (dMEFs) were changed to the human glioma T98G cell line. Note that, the following viral solutions were used.
[Viral Solution]
(1) pMX-GFP vector-derived viral solution (control)
(2) pMX-human GLIS1 vector-derived viral solution, pMX-human Neurogenin3 vector-derived viral solution, pMX-human Pdx1 vector-derived viral solution, and pMX-human MafA vector-derived viral solution
(3) pMX-human mutated GLIS1 vector-derived viral solution, pMX-human Neurogenin3 vector-derived viral solution, pMX-human Pdx1 vector-derived viral solution, and pMX-human MafA vector-derived viral solution
(4) pMX-human mutated GLIS1 vector-derived viral solution, pMX-human Neurogenin3 vector-derived viral solution, and pMX-human MafA vector-derived viral solution
(5) pMX-human mutated GLIS1 vector-derived viral solution, pMX-human Neurogenin3 vector-derived viral solution, and pMX-human Pdx1 vector-derived viral solution
<Quantitative PCR Analysis>
The quantitative PCR analysis was performed in the same manner as in the Test Example 7.

Figure 8:
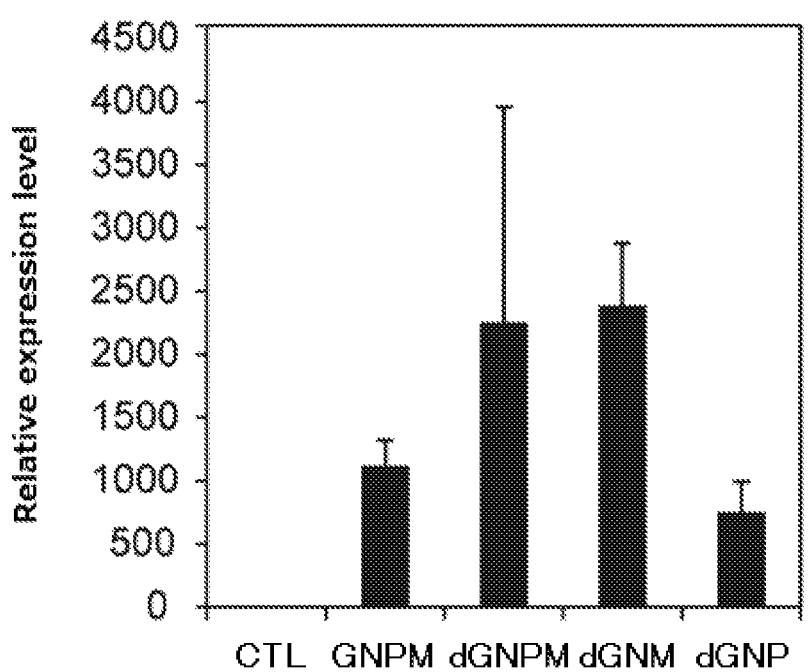
FIG. 8 is a graph illustrating the measurement results of a relative expression level of an insulin gene in Test Example 8.

The results are presented in FIG. 8. In FIG. 8, "CTL" represents the result in the case of using the (1) pMX-GFP vector-derived viral solution (control), "GNPM" represents the result in the case of using the (2) pMX-human GLIS1 vector-derived viral solution, pMX-human Neurogenin3 vector-derived viral solution, pMX-human Pdx1 vector-derived viral solution, and pMX-human MafA vector-derived viral solution, "dGNPM" represents the result in the case of using the (3) pMX-human mutated GLIS1 vector-derived viral solution, pMX-human Neurogenin3 vector-derived viral solution, pMX-human Pdx1 vector-derived viral solution, and pMX-human MafA vector-derived viral solution, "dGNM" represents the result in the case of using the (4) pMX-human mutated GLIS1 vector-derived viral solution, pMX-human Neurogenin3 vector-derived viral solution, and pMX-human MafA vector-derived viral solution, and "dGNP" represents the result in the case of using the (5) pMX-human mutated GLIS1 vector-derived viral solution, pMX-human Neurogenin3 vector-derived viral solution, and pMX-human Pdx1 vector-derived viral solution.

It was demonstrated from the results of FIG. 8 that, the pancreatic endocrine cells were able to be produced efficiently using human cells in any case where factors according to any of aspects of the method of the present invention were used.

A method for producing pancreatic endocrine cells according to the present invention is simple and is easily reproduced compared to previous methods in which pancreatic endocrine cells are produced using ES cells or iPS cells under a culturing environment properly adjusted, for example, by adding a development inhibitor to a medium. According to the method of the present invention, the pancreatic endocrine cells are capable of being very efficiently produced. Moreover, the pancreatic endocrine cells are capable of being produced in a much shorter period of time.

The method of the present invention is also advantageous in that the pancreatic endocrine cells are capable of being produced without undergoing the iPS cell stage that has a risk of forming tumors.

Therefore, the method for producing pancreatic endocrine cells according to the present invention is suitably available for, for example, producing pancreatic endocrine cells to be used in regenerative therapies for diabetes.

Aspects of the present invention are, for example, as follows.
<1> A method for producing pancreatic endocrine cells, the method including introducing (A), (B), (C), or (D) below into somatic cells:
(A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof;
(B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof;

(C) a GLIS1 gene or one or more gene products thereof, a Neurogenin3 gene or one or more gene products thereof, a Pdx1 gene or one or more gene products thereof, and a MafA gene or one or more gene products thereof; and (D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof.

<2> The method for producing pancreatic endocrine cells according to <1>, wherein the (A), (B), (C), or (D) to be introduced into the somatic cells is (A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof.

<3> The method for producing pancreatic endocrine cells according to <1>, wherein the (A), (B), (C), or (D) to be introduced into the somatic cells is (B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof.

<4> The method for producing pancreatic endocrine cells according to <1>, wherein the (A), (B), (C), or (D) to be introduced into the somatic cells is (C) a GLIS1 gene or one or more gene products thereof, a Neurogenin3 gene or one or more gene products thereof, a Pdx1 gene or one or more gene products thereof, and a MafA gene or one or more gene products thereof.

<5> The method for producing pancreatic endocrine cells according to <1>, wherein the (A), (B), (C), or (D) to be introduced into the somatic cells is (D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof.

<6> The method for producing pancreatic endocrine cells according to any one of <1> to <5>, wherein the somatic cells are fibroblasts or mesenchymal stem cells.

<7> The method for producing pancreatic endocrine cells according to any one of <1> to <6>, wherein the pancreatic endocrine cells are β cells.

<8> A transdifferentiation agent including
(A), (B), (C), or (D) below:
(A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof;

(B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof;

(C) a GLIS1 gene or one or more gene products thereof, a Neurogenin3 gene or one or more gene products thereof, a Pdx1 gene or one or more gene products thereof, and a MafA gene or one or more gene products thereof; and (D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof;

wherein the transdifferentiation agent is configured to transdifferentiate somatic cells into pancreatic endocrine cells.

<9> The transdifferentiation agent according to <8>, wherein the (A), (B), (C), or (D) is (A) a mutated GLIS1 gene having a sequence identity of 85% or more to a base sequence represented by SEQ ID NO: 1 or 2 or one or more gene products thereof, a Neurogenin3 gene or one or more gene products thereof, a Pdx1 gene or one or more gene products thereof, and a MafA gene or one or more gene products thereof.

<10> The transdifferentiation agent according to <8>, wherein the (A), (B), (C), or (D) is (B) a mutated GLIS1 gene having a sequence identity of 85% or more to a base sequence represented by SEQ ID NO: 1 or 2 or one or more gene products thereof, a Neurogenin3 gene or one or more gene products thereof, and a Pdx1 gene or one or more gene products thereof.

<11> The transdifferentiation agent according to <8>, wherein the (A), (B), (C), or (D) is (C) a GLIS1 gene or one or more gene products thereof, a Neurogenin3 gene or one or more gene products thereof, a Pdx1 gene or one or more gene products thereof, and a MafA gene or one or more gene products thereof.

<12> The transdifferentiation agent according to <8>, wherein the (A), (B), (C), or (D) is (D) a mutated GLIS1 gene having a sequence identity of 85% or more to a base sequence represented by SEQ ID NO: 1 or 2 or one or more gene products thereof, a Neurogenin3 gene or one or more gene products thereof, and a MafA gene or one or more gene products thereof.

<13> The transdifferentiation agent according to any one of <8> to <12>, wherein the somatic cells are fibroblasts or mesenchymal stem cells.

<14> The transdifferentiation agent according to any one of <8> to <13>, wherein the pancreatic endocrine cells are β cells.

The invention claimed is:

1. A method for producing pancreatic endocrine cells, the method comprising:

introducing a GLIS1 gene or one or more gene products thereof, a Neurogenin 3 gene or one or more gene products thereof, a Pdx 1 gene or one or more gene products thereof, and a MafA gene or one or more gene products thereof into cultured somatic cells to transdifferentiate into a population of pancreatic endocrine cells comprising insulin-producing beta-cells, wherein the GLIS1 gene comprises the nucleotide sequence as set forth in SEQ ID NO:1 or SEQ ID NO:2, and wherein the population of pancreatic endocrine cells are produced without undergoing an induced pluripotent stem (iPS) cell stage.

2. The method for producing pancreatic endocrine cells according to claim 1, wherein the somatic cells are fibroblasts or mesenchymal stem cells.

* * * * *